(12) United States Patent  
Frank et al.

(10) Patent No.: US 8,252,816 B2  
(45) Date of Patent: *Aug. 28, 2012

(54) VANILLOID RECEPTOR LIGAND COMPOUNDS, PHARMACEUTICAL COMPOSITIONS CONTAINING THEM, A METHOD OF PRODUCING THEM AND THE USE THEREOF TO TREAT PAIN AND VARIOUS OTHER CONDITIONS

(75) Inventors: Robert Frank, Aachen (DE); Gregor Bahrenberg, Aachen (DE); Thomas Christoph, Aachen (DE); Klaus Schiene, Juechen (DE); Jean De Vry, Stolberg (DE); Derek Saunders, Aachen (DE); Jeewoo Lee, Ansan-Si (KR)

(73) Assignee: Gruenenthal GmbH, Aachen (DE)

( * ) Notice: Subject to any disclaimer, the term of this patent is extended or adjusted under 35 U.S.C. 154(b) by 1058 days.

This patent is subject to a terminal disclaimer.

(21) Appl. No.: 12/081,174

(22) Filed: Apr. 11, 2008

(65) Prior Publication Data

US 2008/0269289 A1 Oct. 30, 2008

(30) Foreign Application Priority Data

Apr. 13, 2007 (DE) .......................... 10 2007 017 884

(51) Int. Cl.  
*A61K 31/445* (2006.01)  
*C07D 211/14* (2006.01)

(52) U.S. Cl. ............... 514/331; 514/212; 514/237.8; 514/255; 514/318; 540/311; 544/106; 544/124; 546/193; 546/229; 548/565

(58) Field of Classification Search .............. 514/212, 514/237.8, 255, 318, 331, 605; 540/311; 544/106, 124; 546/193, 229; 548/565; 564/99  
See application file for complete search history.

(56) References Cited

U.S. PATENT DOCUMENTS

2007/0105861 A1* 5/2007 Lee et al. .......................... 514/241  
2009/0137594 A1 5/2009 Frank et al.

FOREIGN PATENT DOCUMENTS

WO WO 2005/003084 A1 1/2005  
WO WO 2006/122773 A1 11/2006  
WO WO 2007/045462 A2 4/2007

OTHER PUBLICATIONS

Barber et al. "Effects of . . . " CA131:139345 (1999).*  
Dorwald F. A. Side Reactions in Organic Synthesis, 2005, Wiley: VCH, Weinheim p. IX of Preface p. 1-15.*  
Yvonne C.Martin et. al. "Do Structurally Similar Molecules Have Similar Biological Activity?" Journal of Medicinal Chemistry 2002, 45, 4350-4358.*  
Swanson et. al. "Identification and Biological Evaluation of 4-(3-Trifluoromethylpyridin-2-yl)piperazine-l-carboxylic Acid (5-Trifluoromethylpyridin-2-yl)amide, a High Affinity TRPV1 (VR1) Vanilloid Receptor Antagonist" Journal of Medicinal Chemistry 2005, 48, 1857-1872.*  
Exhibit I (2011).*  
Wilkipedia "TRPV1" p. 1-8 (2012).*  
International Search Report dated Jun. 25, 2008 with English translation (Four (4) pages).  
International Preliminary Report on Patentability dated Nov. 10, 2009 with English translation (Eighteen (18) pages).

* cited by examiner

Primary Examiner — Celia Chang  
(74) Attorney, Agent, or Firm — Crowell & Moring LLP

(57) ABSTRACT

Compounds corresponding to formula I:

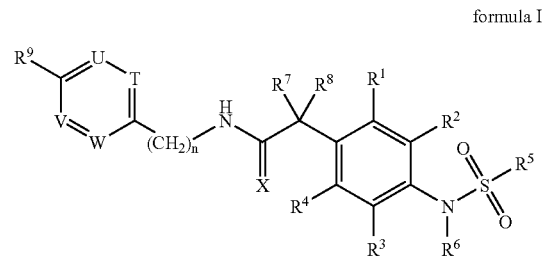

formula I which act as vanilloid receptor ligands, pharmaceutical composition s containing such compounds, a method for producing the compounds, and the use of such compounds to treat pain and various other conditions.

18 Claims, No Drawings

VANILLOID RECEPTOR LIGAND COMPOUNDS, PHARMACEUTICAL COMPOSITIONS CONTAINING THEM, A METHOD OF PRODUCING THEM AND THE USE THEREOF TO TREAT PAIN AND VARIOUS OTHER CONDITIONS

The present invention relates to novel vanilloid receptor ligands, to methods for producing them, to medicaments containing these compounds and to the use of these compounds for the production of medicaments.

The treatment of pain, in particular neuropathic pain, is of great medical significance. There is a worldwide need for effective pain treatments. The urgency of the requirement for effective therapeutic methods for providing tailored and targeted treatment of chronic and non-chronic pain, this being taken to mean pain treatment which is effective and satisfactory from the patient's standpoint, is also evident from the large number of scientific papers relating to applied analgesia and to basic nociception research which have appeared in recent times.

One suitable approach to the treatment of pain, in particular of pain selected from the group consisting of acute pain, chronic pain, neuropathic pain and visceral pain, particularly preferably of neuropathic pain, is the vanilloid receptor subtype 1 (VR1/TRPV1), which is often also known as the capsaicin receptor. This receptor is stimulated inter alia by vanilloids such as for example capsaicin, heat and protons and plays a central role in the genesis of pain. It is furthermore of significance to numerous other physiological and pathophysiological processes, such as for example migraine; depression; neurodegenerative diseases; cognitive disorders; anxiety states; epilepsy; coughing; diarrhoea; pruritus; inflammation; disorders of the cardiovascular system; disorders of food intake; dependency on medicines; abuse of medicines and in particular urinary incontinence.

One object of the present invention was accordingly to provide novel compounds which are suitable in particular as pharmacological active ingredients in medicaments, preferably in medicaments for the treatment of disorders or diseases which are mediated at least in part by vanilloid receptors 1 (VR1/TRPV1 receptors).

It has surprisingly now been found that the substituted compounds of the general formula I stated below display excellent affinity for the vanilloid receptor of the subtype 1 (VR1/TRPV1 receptor) and are therefore suitable in particular for the prevention and/or treatment of disorders or diseases which are mediated at least in part by vanilloid receptors 1 (VR1/TRPV1). Likewise the substituted compounds of the general formula I stated below exhibit antiinflammatory activity.

The present invention accordingly provides substituted compounds of the general formula I

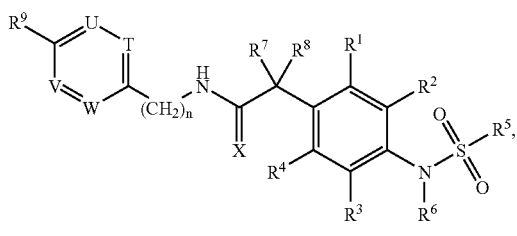

I in which
X denotes O, S or N—C≡N;
n denotes 0, 1, 2, 3 or 4;
$R^1$, $R^2$, $R^3$ and $R^4$, mutually independently, in each case denote H; F; Cl; Br; I; —$SF_5$; —$NO_2$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —$NHR^{10}$; —$NR^{11}R^{12}$; —$OR^{13}$; —$SR^{14}$; —C(=O)—$NHR^{15}$; —C(=O)—$NR^{16}R^{17}$; —S(=O)$_2$—$NHR^{18}$; —S(=O)$_2$—$NR^{19}R^{20}$; —C(=O)—$OR^{21}$; —C(=O)—$R^{22}$; —S(=O)—$R^{23}$; —S(=O)$_2$—$R^{24}$ or denote a linear or branched, saturated or unsaturated, unsubstituted or at least monosubstituted aliphatic $C_{1-10}$ residue;
$R^5$ denotes —$NH_2$; —$NHR^{25}$; —$NR^{26}R^{27}$ or denotes a linear or branched, saturated or unsaturated, unsubstituted or at least monosubstituted aliphatic $C_{1-10}$ residue;
$R^6$ denotes —C(=O)—$R^{28}$ or denotes a linear or branched, saturated or unsaturated, unsubstituted or at least monosubstituted aliphatic $C_{1-10}$ residue;
$R^7$ and $R^8$, mutually independently, in each case denote a hydrogen residue;
  denote a linear or branched, saturated or unsaturated, unsubstituted or at least monosubstituted aliphatic $C_{1-10}$ residue;
  denote an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted $C_{1-6}$ alkylene group or $C_{2-6}$ alkenylene group or $C_{2-6}$ alkynylene group;
  or denote an unsaturated or saturated, unsubstituted or at least monosubstituted 3-, 4-, 5-, 6-, 7-, 8- or 9-membered cycloaliphatic residue optionally comprising at least one heteroatom as a ring member;
providing that $R^7$ and $R^8$ do not in each case denote a hydrogen residue;
or
$R^7$ and $R^8$ in each case together with the carbon atom joining them together as a ring member form a saturated or unsaturated, unsubstituted or at least monosubstituted 3-, 4-, 5- or 6-membered cycloaliphatic residue;
T denotes C—$R^{29}$ and U denotes C—$R^{30}$ and V denotes N and W denotes C—$R^{32}$
or
T denotes C—$R^{29}$ and U denotes N and V denotes C—$R^{31}$ and W denotes C—$R^{32}$
or
T denotes N and U denotes C—$R^{30}$ and V denotes C—$R^{31}$ and W denotes C—$R^{32}$
or
T denotes N and U denotes N and V denotes C—$R^{31}$ and W denotes C—$R^{32}$
or
T denotes N and U denotes C—$R^{30}$ and V denotes N and W denotes C—$R^{32}$
or
T denotes C—$R^{29}$ and U denotes N and V denotes N and W denotes C—$R^{32}$
or
T denotes C—$R^{29}$ and U denotes C—$R^{30}$ and V denotes C—$R^{31}$ and W denotes C—$R^{32}$;
$R^9$ denotes F; Cl; Br; I; —$SF_5$; —$NO_2$; —$CF_3$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —$NHR^{10}$; —$NR^{11}R^{12}$;

—OR$^{13}$; —SR$^{14}$; —C(=O)—NHR$^{15}$; —C(=O)—NR$^{16}$R$^{17}$; —S(=O)$_2$—NHR$^{18}$; —S(=O)$_2$—NR$^{19}$R$^{20}$; —C(=O)—OR$^{21}$; —C(=O)—R$^{22}$; —S(=O)—R$^{23}$; —S(=O)$_2$—R$^{24}$;

denotes a linear or branched, saturated or unsaturated, unsubstituted or at least monosubstituted aliphatic C$_{1-10}$ residue;

or denotes an unsaturated or saturated, unsubstituted or at least monosubstituted 3-, 4-, 5-, 6-, 7-, 8- or 9-membered cycloaliphatic residue optionally comprising at least one heteroatom as a ring member;

R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^{23}$ and R$^{24}$, mutually independently, in each case denote a linear or branched, saturated or unsaturated, unsubstituted or at least monosubstituted aliphatic C$_{1-10}$ residue;

denote an unsaturated or saturated, unsubstituted or at least monosubstituted 3-, 4-, 5-, 6-, 7-, 8- or 9-membered cycloaliphatic residue optionally comprising at least one heteroatom as a ring member, which residue may be fused with a saturated or unsaturated, unsubstituted or at least monosubstituted mono- or polycyclic ring system and/or be attached via a linear or branched, unsubstituted or at least monosubstituted C$_{1-6}$ alkylene group or 2- to 6-membered heteroalkylene group;

or denote an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted C$_{1-6}$ alkylene group or 2- to 6-membered heteroalkylene group;

R$^{25}$, R$^{26}$ and R$^{27}$, mutually independently, in each case denote a linear or branched, saturated or unsaturated, unsubstituted or at least monosubstituted aliphatic C$_{1-10}$ residue;

R$^{28}$ denotes a linear or branched, saturated or unsaturated, unsubstituted or at least monosubstituted aliphatic C$_{1-10}$ residue;

R$^{29}$, R$^{30}$ and R$^{31}$, mutually independently, in each case denote H; F; Cl; Br; I; —SF$_5$; —NO$_2$; —CF$_3$; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{10}$; —NR$^{11}$R$^{12}$; —OR$^{13}$; —SR$^{14}$; —C(=O)—NHR$^{15}$; —C(=O)—NR$^{16}$R$^{17}$; —S(=O)$_2$—NHR$^{18}$; —S(=O)$_2$—NR$^{19}$R$^{20}$; —C(=O)—OR$^{21}$; —C(=O)—R$^{22}$; —S(=O)—R$^{23}$; —S(=O)$_2$—R$^{24}$;

denote a linear or branched, saturated or unsaturated, unsubstituted or at least monosubstituted aliphatic C$_{1-10}$ residue;

or denote an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted C$_{1-6}$ alkylene group or C$_{2-6}$ alkenylene group or C$_{2-6}$ alkynylene group;

R$^{32}$ denotes H; F; Cl; Br; I; —SF$_5$; —NO$_2$; —CF$_3$; —CF$_2$Cl; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{33}$; —NR$^{34}$R$^{35}$; —OR$^{36}$; —SR$^{37}$; —C(=O)—NHR$^{38}$; —C(=O)—NR$^{39}$R$^{40}$; —S(=O)$_2$—NHR$^{41}$; —S(=O)$_2$—NR$^{42}$R$^{43}$; —C(=O)—OR$^{44}$; —C(=O)—R$^{45}$; —S(=O)—R$^{46}$; —S(=O)$_2$—R$^{47}$; —C(=NH)—NH$_2$; —C(=NH)—NH—R$^{48}$; —N=C(NH$_2$)$_2$; —N=C(NHR$^{49}$)(NHR$^{50}$);

denotes a linear or branched, saturated or unsaturated, unsubstituted or at least monosubstituted aliphatic C$_{1-10}$ residue;

denotes an unsaturated or saturated, unsubstituted or at least monosubstituted 3-, 4-, 5-, 6-, 7-, 8- or 9-membered cycloaliphatic residue optionally comprising at least one heteroatom as a ring member, which residue is in each case attached to the parent structure via a carbon atom in the ring of the cycloaliphatic residue and may be fused with a saturated or unsaturated, unsubstituted or at least monosubstituted mono- or polycyclic ring system and/or be attached via a linear or branched, unsubstituted or at least monosubstituted C$_{1-6}$ alkylene group or C$_{2-6}$ alkenylene group or C$_{2-6}$ alkynylene group;

or denotes an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted C$_{1-6}$ alkylene group or C$_{2-6}$ alkenylene group or C$_{2-6}$ alkynylene group;

R$^{33}$, R$^{34}$, R$^{35}$, R$^{36}$, R$^{37}$, R$^{38}$, R$^{39}$, R$^{40}$, R$^{41}$, R$^{42}$, R$^{43}$, R$^{44}$, R$^{45}$, R$^{46}$, R$^{47}$, R$^{48}$, R$^{49}$ and R$^{50}$, mutually independently, in each case denote a linear or branched, saturated or unsaturated, unsubstituted or at least monosubstituted aliphatic C$_{1-10}$ residue;

denote an unsaturated or saturated, unsubstituted or at least monosubstituted 3-, 4-, 5-, 6-, 7-, 8- or 9-membered cycloaliphatic residue optionally comprising at least one heteroatom as a ring member, which residue may be fused with a saturated or unsaturated, unsubstituted or at least monosubstituted mono- or polycyclic ring system and/or be attached via a linear or branched, unsubstituted or at least monosubstituted C$_{1-6}$ alkylene group or 2- to 6-membered heteroalkylene group;

or denote an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted C$_{1-6}$ alkylene group or 2- to 6-membered heteroalkylene group;

or

R$^{34}$ and R$^{35}$ in each case together with the nitrogen atom joining them together as a ring member form a saturated or unsaturated or unsubstituted heterocycloaliphatic residue or a 4-, 5-, 6-, 7-, 8- or 9-membered heterocycloaliphatic residue substituted with 1, 2, 3, 4 or 5 residues R$^{51}$ and optionally comprising at least one further heteroatom as a ring member, which heterocycloaliphatic residue may be fused with a saturated or unsaturated, unsubstituted or at least monosubstituted mono- or polycyclic ring system;

R$^{51}$ denotes —NHR$^{52}$, —NR$^{53}$R$^{54}$ or denotes a linear or branched, saturated or unsaturated, unsubstituted or at least monosubstituted aliphatic C$_{1-10}$ residue;

R$^{52}$, R$^{53}$ and R$^{54}$, mutually independently, in each case denote —C(=O)—R$^{55}$; denote a linear or branched, saturated or unsaturated, unsubstituted or at least monosubstituted aliphatic C$_{1-10}$ residue;

or denote an unsubstituted or at least monosubstituted 5- to 14-membered aryl or heteroaryl residue, which may be fused with a saturated or unsaturated, unsubstituted or at least monosubstituted mono- or polycyclic ring system and/or be attached via a linear or branched, unsubstituted or at least monosubstituted C$_{1-6}$ alkylene group or C$_{2-6}$ alkenylene group or C$_{2-6}$ alkynylene group;

and

R$^{55}$ denotes a linear or branched, saturated or unsaturated, unsubstituted or at least monosubstituted aliphatic C$_{1-10}$ residue;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates;

wherein the above-stated aliphatic C$_{1-10}$ residues may optionally in each case be substituted with 1, 2, 3, 4, 5, 6, 7, 8 or 9 substituents mutually independently selected from the group consisting of F, Cl, Br, I, —CN, —NO$_2$, —OH, —NH$_2$, —SH, —O(C$_{1-5}$-alkyl), —S(C$_{1-5}$-alkyl), —NH(C$_{1-5}$-alkyl), —N(C$_{1-5}$-alkyl)(C$_{1-5}$-alkyl), —C(=O)—O—C$_{1-5}$-alkyl, —O—C(=O)—C$_{1-5}$-alkyl, —O-phenyl, phenyl, —OCF$_3$ and —SCF$_3$;

the above-stated 2- to 6-membered heteroalkylene groups, C$_{1-6}$ alkylene groups and C$_{2-6}$ alkenylene groups and C$_{2-6}$ alkynylene groups may optionally in each case be substituted with 1, 2, 3, 4, 5, 6, 7, 8 or 9 substituents mutually independently selected from the group consisting of F, Cl, Br, I, —CN, —NO$_2$, —OH, —NH$_2$, —SH, —O(C$_{1-5}$-alkyl), —S(C$_{1-5}$-alkyl), —NH(C$_{1-5}$-alkyl), —N(C$_{1-5}$-alkyl)(C$_{1-5}$-alkyl), —OCF$_3$ and —SCF$_3$;

the above-stated heteroalkylene groups may in each case optionally comprise 1, 2 or 3 heteroatom(s) mutually independently selected from the group consisting of oxygen, sulfur and nitrogen (NH) as chain link(s);

the above-stated (hetero)cycloaliphatic residues may optionally in each case be substituted with 1, 2, 3, 4 or 5 substituents mutually independently selected from the group consisting of —C$_{1-6}$-alkylene-OH, =CH$_2$, —O—C$_{1-5}$-alkylene-oxetanyl, —C$_{1-5}$-alkylene-O—C$_{1-5}$-alkylene-oxetanyl, —CH$_2$—NH—C$_{1-5}$-alkyl, —CH$_2$—N(C$_{1-5}$-alkyl)$_2$, —N[—C(=O)—C$_{1-5}$-alkyl]-phenyl, —CH$_2$—O—C$_{1-5}$-alkyl, oxo (=O), thioxo (=S), F, Cl, Br, I, —CN, —CF$_3$, —SF$_5$, —OH, —O—C$_{1-5}$-alkyl, —O—C(=O)—C$_{1-5}$-alkyl, —NH$_2$, —NO$_2$, —O—CF$_3$, —S—CF$_3$, —SH, —S—C$_{1-5}$-alkyl, —C$_{1-5}$ alkyl, —C(=O)—C$_{1-5}$-alkyl, —C(=O)—OH, —C(=O)—O—C$_{1-5}$-alkyl, —NH—C$_{1-5}$-alkyl, —N(C$_{1-5}$-alkyl)$_2$, —NH-phenyl, —N(—C$_{1-5}$-alkyl)-phenyl, cyclohexyl, cyclopentyl, (4,5)-dihydroisoxazolyl, thiazolyl, (1,2,5)-thiadiazolyl, thiophenyl, phenethyl, piperidinyl, pyrrolidinyl, —(CH$_2$)-pyridinyl, pyridinyl, —O-phenyl, —O-benzyl, phenyl and benzyl, wherein in each case the cyclic moiety of the residues oxetanyl, (4,5)-dihydroisoxazolyl, thiazolyl, (1,2,5)-thiadiazolyl, thiophenyl, phenethyl, —N[—C(=O)—C$_{1-5}$-alkyl]-phenyl, —NH-phenyl, —N(—C$_{1-5}$-alkyl)-phenyl, —(CH$_2$)-pyridinyl, pyridinyl, —O-phenyl, —O-benzyl, phenyl and benzyl may be substituted with 1, 2, 3, 4 or 5 substituents mutually independently selected from the group consisting of F, Cl, Br, —OH, —CF$_3$, —SF$_5$, —CN, —NO$_2$, —C$_{1-5}$ alkyl, —O—C$_{1-5}$-alkyl, —O—CF$_3$, —S—CF$_3$, phenyl and —O-benzyl, and unless otherwise stated the above-stated (hetero)cycloaliphatic residues may in each case optionally comprise 1, 2 or 3 (further) heteroatom(s) mutually independently selected from the group consisting of oxygen, nitrogen and sulfur;

the rings of the above-stated mono- or polycyclic ring systems may in each case optionally be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, —C$_{1-5}$ alkyl, —C(=O)—C$_{1-5}$-alkyl, —C(=O)—OH, —C(=O)—O—C$_{1-5}$-alkyl, —NH—C$_{1-5}$-alkyl, —N(C$_{1-5}$-alkyl)$_2$, —O-phenyl, —O-benzyl, phenyl and benzyl, wherein in each case the cyclic moiety of the residues —O-phenyl, —O-benzyl, phenyl and benzyl may be substituted with 1, 2, 3, 4 or 5 substituents mutually independently selected from the group consisting of F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl, and the rings of the above-stated mono- or polycyclic ring systems are in each case 5-, 6- or 7-membered and may in each case optionally comprise 1, 2, 3, 4 or 5 heteroatom(s) as ring member(s), which are mutually independently selected from the group consisting of oxygen, nitrogen and sulfur;

and the above-stated aryl or heteroaryl residues may optionally in each case be substituted with 1, 2, 3, 4 or 5 substituents mutually independently selected from the group consisting of F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, —C$_{1-5}$-alkyl, —C(=O)—OH, —C(=O)—O—C$_{1-5}$-alkyl, —NH—C$_{1-5}$-alkyl, —N(C$_{1-5}$-alkyl)$_2$, —NH—S(=O)$_2$—C$_{1-5}$-alkyl, —NH—C(=O)—O—C$_{1-5}$-alkyl, —C(=O)—H, —C(=O)—C$_{1-5}$-alkyl, —C(=O)—NH$_2$, —C(=O)—NH—C$_{1-5}$-alkyl, —C(=O)—N—(—C$_{1-5}$-alkyl)$_2$, —O-phenyl, —O-benzyl, phenyl and benzyl, wherein in each case the cyclic moiety of the residues —O-phenyl, —O-benzyl, phenyl and benzyl may be substituted with 1, 2, 3, 4 or 5 substituents mutually independently selected from the group consisting of F, Cl, Br, —OH, —CF$_3$, —SF$_5$, —CN, —NO$_2$, —C$_{1-5}$ alkyl, —O—C$_{1-5}$-alkyl, —O—CF$_3$, —S—CF$_3$, phenyl and —O-benzyl, and the above-stated heteroaryl residues may in each case optionally comprise 1, 2, 3, 4 or 5 heteroatom(s) mutually independently selected from the group consisting of oxygen, nitrogen and sulfur as ring member(s).

The term "heteroalkylene" denotes an alkylene chain in which one or more C atoms have in each case been replaced by a heteroatom mutually independently selected from the group consisting of oxygen, sulfur and nitrogen (NH). Heteroalkylene groups may preferably comprise 1, 2 or 3 heteroatom(s), particularly preferably one heteroatom, mutually independently selected from the group consisting of oxygen, sulfur and nitrogen (NH) as chain link(s). Heteroalkylene groups may preferably be 2- to 6-membered, particularly preferably 2- or 3-membered.

Examples which may be mentioned of heteroalkylene groups are —CH$_2$—CH$_2$—O—CH$_2$—, —CH$_2$—CH(CH$_3$)—O—CH$_2$—, —(CH$_2$)—O—, —(CH$_2$)$_2$—O—, —(CH$_2$)$_3$—O—, —(CH$_2$)$_4$—O—, —O—(CH$_2$)—, —O—(CH$_2$)$_2$—, —O—(CH$_2$)$_3$—, —O—(CH$_2$)$_4$—, —C(C$_2$H$_5$)(H)—O—, —O—C(C$_2$H$_5$)(H)—, —CH$_2$—O—CH$_2$—, —CH$_2$—S—CH$_2$—, —CH$_2$—NH—CH$_2$—, —CH$_2$—NH— and —CH$_2$—CH$_2$—NH—CH$_2$—CH$_2$.

If one or more of the above-stated substituents comprise a linear or branched C$_{1-6}$ alkylene group, this may preferably be selected from the group consisting of —(CH$_2$)—, —(CH$_2$)$_2$—, —C(H)(CH$_3$)—, —(CH$_2$)$_3$—, —(CH$_2$)$_4$—, —(CH$_2$)$_5$—, —C(H)(C(H)(CH$_3$)$_2$)- and —C(C$_2$H$_5$)(H)—.

Saturated or unsaturated C$_{1-10}$ aliphatic residues may denote a —C$_{1-10}$ alkyl, C$_{2-10}$ alkenyl or C$_{2-10}$ alkynyl residue. C$_{2-10}$ alkenyl residues comprise at least one, preferably 1, 2, 3 or 4 C—C double bonds and C$_{2-10}$ alkynyl residues comprise at least one, preferably 1, 2 3 or 4 C—C triple bonds.

Preferred $C_{1-10}$ alkyl residues are those selected from the group consisting of methyl, ethyl, n-propyl, isopropyl, n-butyl, sec.-butyl, isobutyl, tert.-butyl, n-pentyl, 3-methyl-but-1-yl, 2-pentyl, 3-pentyl, sec.-pentyl, neopentyl, 4-methyl-pent-1-yl, (3,3)-dimethyl-but-1-yl, n-hexyl, n-heptyl, 2-heptyl, 3-heptyl, 4-heptyl, n-octyl, n-nonyl, 2-nonyl, 3-nonyl, 4-nonyl, 5-nonyl and (2,6)-dimethyl-hept-4-yl, which may optionally be substituted with 1, 2, 3, 4, 5, 6, 7, 8 or 9 substituents mutually independently selected from the group consisting of —O-phenyl, —O—C(=O)—CH$_3$, —O—C(=O)—C$_2$H$_5$, —O—C(=O)—CH(CH$_3$)$_2$, —O—C(=O)—C(CH$_3$)$_3$, —C(=O)—O—CH$_3$, —C(=O)—O—C$_2$H$_5$, —C(=O)—O—CH(CH$_3$)$_2$, —C(=O)—O—C(CH$_3$)$_3$, F, Cl, Br, I, —CN, —NO$_2$, —OH, —NH$_2$, —SH, —O—CH$_3$, —O—C$_2$H$_5$, —O—CH(CH$_3$)$_2$, —O—C(CH$_3$)$_3$, —S—CH$_3$, —S—C$_2$H$_5$, —S—CH(CH$_3$)$_2$, —S—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —OCF$_3$ and —SCF$_3$.

Likewise preferred $C_{2-10}$ alkenyl residues are those selected from the group consisting of vinyl, 1-propenyl, 2-propenyl, 1-butenyl, 2-butenyl, 3-butenyl, 2-methyl-propen-1-yl, 3-methyl-but-2-en-1-yl, (3,3)-dimethyl-but-1-enyl, 2-methyl-buten-2-yl, 1-pentenyl, 2-pentenyl, 3-pentenyl, 4-pentenyl, 1-hexenyl, 1-heptenyl and 1-octenyl, which may optionally be substituted with 1, 2 or 3 substituents mutually independently selected from the group consisting of F, Cl, Br, I, —CN, —NO$_2$, —OH, —NH$_2$, —SH, —O—CH$_3$, —O—C$_2$H$_5$, —O—CH(CH$_3$)$_2$, —O—C(CH$_3$)$_3$, —S—CH$_3$, —S—C$_2$H$_5$, —S—CH(CH$_3$)$_2$, —S—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —OCF$_3$ and —SCF$_3$.

Also preferred are $C_{2-10}$ alkynyl residues selected from the group consisting of (3,3)-dimethyl-but-1-ynyl, 4-methyl-pent-1-ynyl, 1-hexynyl, ethynyl, 1-propynyl, 2-propynyl, 1-butynyl, 2-butynyl, 3-butynyl, 1-pentynyl, 2-pentynyl, 3-pentynyl and 4-pentynyl, which may optionally be substituted with 1, 2 or 3 substituents mutually independently selected from the group consisting of F, Cl, Br, I, —CN, —NO$_2$, —OH, —NH$_2$, —SH, —O—CH$_3$, —O—C$_2$H$_5$, —O—CH(CH$_3$)$_2$, —O—C(CH$_3$)$_3$, —S—CH$_3$, —S—C$_2$H$_5$, —S—CH(CH$_3$)$_2$, —S—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —OCF$_3$ and —SCF$_3$.

Particularly preferred optionally substituted $C_{1-10}$ aliphatic residues are those selected from the group consisting of methyl, —CF$_3$, —CHF$_2$, —CH$_2$F, —CF$_2$Cl, —CCl$_2$F, —CCl$_3$, —CBr$_3$, —CH$_2$—CN, —CH$_2$—O—CH$_3$, —CH$_2$—O—CF$_3$, —CH$_2$—SF$_3$, —CH$_2$—NH$_2$, —CH$_2$—OH, —CH$_2$—SH, —CH$_2$—NH—CH$_3$, —CH$_2$—N(CH$_3$)$_2$, —CH$_2$—N(C$_2$H$_5$)$_2$, —CH$_2$—N(CH$_3$)(C$_2$H$_5$), ethyl, —CF$_2$—CH$_3$, —CHF—CF$_2$Cl, —CF$_2$—CFCl$_2$, —CFCl—CF$_2$Cl, —CFCl—CFCl$_2$, —CH$_2$—CH$_2$—NH$_2$, —CH$_2$—CH$_2$—OH, —CH$_2$—CH$_2$—SH, —CH$_2$—CH$_2$—NH—CH$_3$, —CH$_2$—CH$_2$—N(CH$_3$)$_2$, —CH$_2$—CH$_2$—N(C$_2$H$_5$)$_2$, —CH$_2$—CH$_2$—N(CH$_3$)(C$_2$H$_5$), —CH$_2$—CF$_3$, —C$_2$F$_5$, —CH$_2$—CCl$_3$, —CH$_2$—CBr$_3$, —CH$_2$—CH$_2$—CN, n-propyl, —CH$_2$—CH$_2$—CH$_2$—OH, —CH$_2$—CH$_2$—CH$_2$—SH, —CH$_2$—CH$_2$—CH$_2$—NH$_2$, —CH$_2$—CH$_2$—CH$_2$—NH—CH$_3$, —CH$_2$—CH$_2$—CH$_2$—N(CH$_3$)$_2$, —CH$_2$—CH$_2$—CH$_2$—N(C$_2$H$_5$)$_2$, —CH$_2$—CH$_2$—CH$_2$—N(CH$_3$)(C$_2$H$_5$), —CH$_2$—CH$_2$—O—CH$_3$, —CF$_2$—CF$_2$—CF$_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SF$_3$, —CH$_2$—CH$_2$—OCF$_3$, —CH(CH$_3$)(O—CH$_3$), —CH(CH$_3$)(S—CH$_3$), n-butyl, —CF$_2$—CF$_2$—CF$_2$—CF$_3$, —CH$_2$—CH$_2$—CH$_2$—CN, —CH$_2$—CH$_2$—CH$_2$—CF$_3$, —CH$_2$—CH$_2$—CH$_2$—CF$_3$, —CH$_2$—O—C(=O)—CH$_3$, —CH$_2$—O—C(=O)—C$_2$H$_5$, —CH$_2$—O—C(=O)—CH(CH$_3$)$_2$, —CH$_2$—O—C(=O)—C(CH$_3$)$_3$, —CH$_2$—C(=O)—O—CH$_3$, —CH$_2$—C(=O)—O—C$_2$H$_5$, —CH$_2$—C(=O)—O—CH(CH$_3$)$_2$, —CH$_2$—C(=O)—O—C(CH$_3$)$_3$, —CH$_2$—CH$_2$—O—CH$_3$, —CH$_2$—CH$_2$—O—C$_2$H$_5$, —CH$_2$—CH$_2$—O-phenyl, —CH$_2$—CH$_2$—CH$_2$—O—CH$_3$, sec.-butyl, isobutyl, tert.-butyl, n-pentyl, sec.-pentyl, neopentyl, n-hexyl, vinyl, 1-propenyl, 2-propenyl, 1-butenyl, 2-butenyl, 3-butenyl, 2-methyl-buten-2-yl, (1,1,2)-trifluoro-1-butenyl, 1-pentenyl, 2-pentenyl, 3-pentenyl, 4-pentenyl, —CF=CF$_2$, —CCl=CCl$_2$, —CH$_2$—CF=CF$_2$, —CH$_2$—CCl=CCl$_2$, —C≡C—I, —C≡C—F and —C≡C—Cl.

If one or more of the above-stated substituents denote a (hetero)cycloaliphatic residue, which may optionally be fused with a saturated or unsaturated, unsubstituted or at least monosubstituted mono- or polycyclic ring system, the latter may preferably be selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, oxetanyl, (1,2,3,6)-tetrahydropyridinyl, azepanyl, azocanyl, diazepanyl, dithiolanyl, (1,3,4,5)-tetrahydropyrido[4,3-b]indolyl, (3,4)-dihydro-1H-isoquinolinyl, (1,3,4,9)-tetrahydro-[b]-carbolinyl and (1,3)-thiazolidinyl.

Examples which may be mentioned of suitable (hetero)cycloaliphatic residues, which may unsubstituted or mono- or polysubstituted and are fused with a mono- or bicyclic ring system, are (4,5,6,7)-tetrahydroisoxazolo[5,4-c]pyridinyl, (2,3)-dihydro-1H-indenyl, 3-aza-bicyclo[3.1.1]heptyl, 3-aza-bicyclo[3.2.1]octyl, 6-aza-bicyclo[3.3.1]heptyl, 8-aza-bicyclo[3.2.1]octyl, isoindolyl, indolyl, (1,2,3,4)-tetrahydroquinolinyl, (1,2,3,4)-tetrahydroisoquinolinyl, (2,3)-dihydro-1H-isoindolyl, (1,2,3,4)-tetrahydronaphthyl, (2,3)-dihydro-benzo[1.4]dioxinyl, benzo[1.3]dioxolyl, (1,4)-benzodioxanyl, (2,3)-dihydrothieno[3,4-b][1,4]dioxinyl, (3,4)-dihydro-2H-benzo[1.4]oxazinyl, octahydro-1H-isoindolyl and octahydro-pyrrolo[3,4-c]pyrrolyl.

For the purposes of the present invention, (hetero)cycloaliphatic residues may, together with a further (hetero)cycloaliphatic residue, form a spirocyclic residue by way of a common carbon atom in the two rings.

Suitable spirocyclic residues which may be mentioned are, for example, a 6-aza-spiro[2.5]octyl residue, 8-azaspiro[4.5] decyl residue and a 1-oxa-2,8-diaza-spiro[4.5]dec-2-enyl residue.

The (hetero)cycloaliphatic residues may particularly preferably optionally in each case be substituted with 1, 2, 3, 4 or 5 substituents mutually independently selected from the group consisting of oxo (=O), thioxo (=S), F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec.-butyl, isobutyl, tert.-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —CH$_2$—OH, —CH$_2$—CH$_2$—OH, =CH$_2$, —CH$_2$—O—CH$_2$-oxetanyl, —O—CH$_2$-oxetanyl, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, —CH$_2$—O—CH$_3$, —CH$_2$—O—CH$_2$—CH$_3$, —NH-phenyl, —N(CH$_3$)-phenyl, —N($C_2H_5$)-phenyl, —N($C_2H_5$)-phenyl, —O—$CH_2$—$CH_2$—$CH_2$—$CH_3$, (4,5)-dihydroisoxazolyl, thiazolyl, (1,2,5)-thiadiazolyl, thiophenyl, phenethyl, cyclohexyl, cyclopentyl, piperidinyl, pyrrolidinyl, —O—C(=O)—$CH_3$, —O—C(=O)—$C_2H_5$, —O—C(=O)—C($CH_3$)$_3$, —($CH_2$)-pyridinyl, pyridinyl, —O-phenyl, —O-benzyl, phenyl and benzyl, wherein in each case the cyclic moiety of the residues oxetanyl, (4,5)-dihydroisoxazolyl, thiazolyl, (1,2,5)-thiadiazolyl, thiophenyl, phenethyl, —N—[C(=O)—$C_2H_5$]-phenyl, —N—[C(=O)—$CH_3$]-phenyl, —NH-phenyl, —N($CH_3$)-phenyl, —N($C_2H_5$)— phenyl, —($CH_2$)-pyridinyl, pyridinyl, —O-phenyl, —O-benzyl, phenyl and benzyl may be substituted with 1, 2, 3, 4 or 5 substituents mutually independently selected from the group consisting of F, Cl, Br, —OH, —$CF_3$, —$SF_5$, —CN, —$NO_2$, methyl, ethyl, n-propyl, isopropyl, n-butyl, sec.-butyl, isobutyl, tert.-butyl, —O—$CH_3$, —O—$C_2H_5$, —O—CH($CH_3$)$_2$, —O—C($CH_3$)$_3$, —O—$CF_3$, —S—$CF_3$, phenyl and —O-benzyl.

If one or more of the above-stated substituents denote(s) an aryl residue, the latter may preferably be selected from the group consisting of phenyl and naphthyl (1-naphthyl and 2-naphthyl).

If one or more of the above-stated substituents denote(s) a heteroaryl residue, the latter may preferably be selected from the group consisting of tetrazolyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzoxazolyl, benzisoxazolyl, thiazolyl, oxazolyl, isoxazolyl, pyridazinyl, pyrazinyl, pyrimidinyl, indazolyl, quinoxalinyl, quinolinyl and isoquinolinyl.

Examples which may be mentioned of suitable aryl- and heteroaryl residues which may be unsubstituted or mono- or polysubstituted and are fused with a mono- or bicyclic ring system are isoindolyl, indolyl, (1,2,3,4)-tetrahydroquinolinyl, (1,2,3,4)-tetrahydroisoquinolinyl, (2,3)-dihydro-1H-isoindolyl, (1,2,3,4)-tetrahydronaphthyl, (2,3)-dihydrobenzo[1.4]dioxinyl, (2,3)-dihydrothieno[3,4-b)][1,4]dioxinyl, benzo[1.3]dioxolyl, and (1,4)-benzodioxanyl.

The aryl or heteroaryl residues may particularly preferably in each case optionally be substituted with 1, 2, 3, 4 or 5 substituents mutually independently selected from the group consisting of F, Cl, Br, I, —CN, —$CF_3$, —$SF_5$, —OH, —O—$CH_3$, —O—$C_2H_5$, —O—CH($CH_3$)$_2$, —O—C($CH_3$)$_3$, —$NH_2$, —$NO_2$, —O—$CF_3$, —S—$CF_3$, —SH, —S—$CH_3$, —S—$C_2H_5$, —S—CH($CH_3$)$_2$, —S—C($CH_3$)$_3$, methyl, ethyl, n-propyl, isopropyl, n-butyl, sec.-butyl, isobutyl, tert.-butyl, n-pentyl, —C(=O)—OH, —C(=O)—O—$CH_3$, —C(=O)—O—$C_2H_5$, —C(=O)—O—CH($CH_3$)$_2$, —C(=O)—O—C($CH_3$)$_3$, —NH—$CH_3$, —NH—$C_2H_5$, —NH—C($CH_3$)$_3$, —N($CH_3$)$_2$, —N($C_2H_5$)$_2$, —N($CH_3$)($C_2H_5$), —NH—S(=O)$_2$—$CH_3$, —NH—S(=O$_2$)—$C_2H_5$, —NH—S(=O)$_2$—CH($CH_3$)$_2$, —NH—C(=O)—O—$CH_3$, —NH—C(=O)—O—$C_2H_5$, —NH—C(=O)—O—C($CH_3$)$_3$, —C(=O)—H, —C(=O)—$CH_3$, —C(=O)—$C_2H_5$, —C(=O)—CH($CH_3$)$_2$, —C(=O)—C($CH_3$)$_3$, —C(=O)—$NH_2$, —C(=O)—NH—$CH_3$, —C(=O)—NH—$C_2H_5$, —C(=O)—N($CH_3$)$_2$, —C(=O)—N($C_2H_5$)$_2$, —O-phenyl, —O-benzyl, phenyl and benzyl, wherein in each case the cyclic moiety of the residues —O-phenyl, —O-benzyl, phenyl and benzyl may be substituted with 1, 2, 3, 4 or 5 substituents mutually independently selected from the group consisting of F, Cl, Br, —OH, —$CF_3$, —$SF_5$, —CN, —$NO_2$, methyl, ethyl, n-propyl, isopropyl, n-butyl, sec.-butyl, isobutyl, tert.-butyl, —O—$CH_3$, —O—$C_2H_5$, —O—CH($CH_3$)$_2$, —O—C($CH_3$)$_3$, —O—$CF_3$, —S—$CF_3$, phenyl and —O-benzyl.

If a polycyclic ring system, such as for example a bicyclic ring system, is present, the various rings may in each case mutually independently be of a different degree of saturation, i.e. be saturated or unsaturated. A polycyclic ring system is preferably a bicyclic ring system.

Examples of aryl residues which are fused with a mono- or polycyclic ring system and may be mentioned are (1,3)-benzodioxolyl and (1,4)-benzodioxanyl.

If one or more of the above-stated substituents comprise a mono- or polycyclic ring system, the latter may preferably be substituted with 1, 2, 3, 4 or 5 substituents mutually independently selected from the group consisting of oxo (=O), thioxo (=S), F, Cl, Br, I, —CN, —$CF_3$, —$SF_5$, —OH, —O—$CH_3$, —O—$C_2H_5$, —O—CH($CH_3$)$_2$, —O—C($CH_3$)$_3$, —$NH_2$, —$NO_2$, —O—$CF_3$, —S—$CF_3$, —SH, —S—$CH_3$, —S—$C_2H_5$, —S—CH($CH_3$)$_2$, —S—C($CH_3$)$_3$, methyl, ethyl, n-propyl, isopropyl, n-butyl, sec.-butyl, isobutyl, tert.-butyl, n-pentyl, —C(=O)—OH, —C(=O)—O—$CH_3$, —C(=O)—O—$C_2H_5$, —C(=O)—O—CH($CH_3$)$_2$, —C(=O)—O—C($CH_3$)$_3$, —NH—$CH_3$, —NH—$C_2H_5$, —NH—C($CH_3$)$_3$, —N($CH_3$)$_2$, —N($C_2H_5$)$_2$, —N($CH_3$)($C_2H_5$), —NH—C(=O)—O—$CH_3$, —NH—C(=O)—O—$C_2H_5$, —NH—C(=O)—O—C($CH_3$)$_3$, —C(=O)—H, —C(=O)—$CH_3$, —C(=O)—$C_2H_5$, —C(=O)—CH($CH_3$)$_2$, —C(=O)—C($CH_3$)$_3$, —C(=O)—$NH_2$, —C(=O)—NH—$CH_3$, —C(=O)—NH—$C_2H_5$, —C(=O)—N($CH_3$)$_2$, —C(=O)—N($C_2H_5$)$_2$, —O-phenyl, —O-benzyl, phenyl and benzyl, wherein in each case the cyclic moiety of the residues —O-phenyl, —O-benzyl, phenyl and benzyl may be substituted with 1, 2, 3, 4 or 5 substituents mutually independently selected from the group consisting of F, Cl, Br, —OH, —$CF_3$, —$SF_5$, —CN, —$NO_2$, methyl, ethyl, n-propyl, isopropyl, n-butyl, sec.-butyl, isobutyl, tert.-butyl, —O—$CH_3$, —O—$C_2H_5$, —O—CH($CH_3$)$_2$, —O—C($CH_3$)$_3$, —O—$CF_3$, —S—$CF_3$, phenyl and —O-benzyl.

Preference is given to $C_{2-6}$ alkenylene groups such as —CH=CH— and —$CH_2$—CH=CH—.

Preference is given to $C_{2-3}$ alkynylene groups such as —C≡C— and —$CH_2$—C≡C—.

Preferred compounds are those of the above-stated general formula I, in which

X denotes O;

n denotes 0, 1 or 2;

$R^1$, $R^2$, $R^3$ and $R^4$, mutually independently, in each case denote H; F; Cl; Br; I; —$SF_5$; —$NO_2$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —NH$R^{10}$; —$NR^{11}R^{12}$; —$OR^{13}$; —$SR^{14}$; —S(=O)—$R^{23}$; —S(=O)$_2$—$R^{24}$ or denote a residue selected from the group consisting of methyl, —$CF_3$, —$CCl_3$, —$CBr_3$, —$CHF_2$, —$CH_2F$, —$CF_2Cl$, —$CCl_2F$, ethyl, —$CF_2$—$CH_3$, —$CH_2$—$CF_3$, —$C_2F_5$, —$CH_2$—$CCl_3$, —$CH_2$—$CBr_3$, —CHF—$CF_2Cl$, —$CF_2$—$CF_2Cl$, —CFCl—$CF_2Cl$, n-propyl, —$CF_2$—$CF_2$—$CF_3$, —CF($CF_3$)$_2$, isopropyl, n-butyl, sec.-butyl, isobutyl and tert.-butyl;

$R^5$ denotes —$NH_2$; —NH$R^{25}$; —$NR^{26}R^{27}$; denotes an alkyl residue selected from the group consisting of —$CF_3$, —$CH_2$—$CF_3$, methyl, ethyl, n-propyl, isopropyl, tert.-butyl, n-butyl, sec.-butyl and isobutyl;

$R^6$ denotes —C(=O)—$R^{28}$ or denotes a residue selected from the group consisting of methyl, —$CF_3$, —$CCl_3$, —$CBr_3$, —$CHF_2$, —$CH_2F$, —$CF_2Cl$, —$CCl_2F$, —$CH_2$—CN, —$CH_2$—O—$CH_3$, —$CH_2$—O—$CF_3$, —$CH_2$—$SF_3$, ethyl, —$CF_2$—$CH_3$, —$CH_2$—$CF_3$, —$C_2F_5$, —$CH_2$—$CCl_3$, —$CH_2$—$CBr_3$, —CHF—$CF_2Cl$, —$CF_2$—$CF_2Cl$, —CFCl—$CF_2Cl$, —$CH_2$—$CH_2$—CN, n-propyl, —$CF_2$—$CF_2$—$CF_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SF$_3$, —CH$_2$—CH$_2$—OCF$_3$, —CH(CH$_3$)(O—CH$_3$), —CH(CH$_3$)(S—CH$_3$), n-butyl, —CF$_2$—CF$_2$—CF$_2$—CF$_3$, —CH$_2$—CH$_2$—CH$_2$—CH$_2$—CN, sec.-butyl, isobutyl, tert.-butyl, n-pentyl, 3-pentyl, n-heptyl, 4-heptyl, n-octyl, n-nonyl, 5-nonyl, (2,6)-dimethyl-hept-4-yl, 3-methylbutyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—CH$_2$—O—CH$_3$, ethenyl, propenyl, 2-butenyl, 3-butenyl, 2-pentenyl and 3-pentenyl;

R$^7$ and R$^8$, mutually independently, in each case denote a hydrogen residue;

denote an alkyl residue selected from the group consisting of —CH$_2$—OH, —CH$_2$—CH$_2$—OH, —CH$_2$—CH$_2$—CH$_2$—OH, —CH$_2$—CH$_2$—CH$_2$—CH$_2$—OH, isopropyl, n-butyl, sec.-butyl, isobutyl, methyl, ethyl and n-propyl;

denote a residue selected from the group consisting of phenyl, naphthyl, thiophenyl, furanyl, pyrrolyl, pyrazolyl, pyrazinyl, pyranyl, triazolyl, pyridinyl, imidazolyl, indolyl, isoindolyl, thiazolyl, oxazolyl, isoxazolyl, pyridazinyl, pyrazinyl, pyrimidinyl, indazolyl, quinoxalinyl, quinolinyl and isoquinolinyl, which may in each case be attached via a —(CH$_2$)—, —(CH$_2$)$_2$— or —(CH$_2$)$_3$— group and/or may in each case be unsubstituted or optionally substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec.-butyl, isobutyl, tert.-butyl and n-pentyl;

or denote a residue selected from the group consisting of cyclopropyl, cyclobutyl, cyclopentyl, cyclohexyl and cycloheptyl;

providing that R$^7$ and R$^8$ do not in each case denote a hydrogen residue;

or

R$^7$ and R$^8$ in each case together with the carbon atom joining them together as a ring member form a residue selected from the group consisting of cyclopropyl, cyclobutyl, cyclopentyl, cyclohexyl and cycloheptyl;

T denotes C—R$^{29}$ and U denotes C—R$^{30}$ V denotes N and W denotes C—R$^{32}$ or T denotes C—R$^{29}$ and U denotes N and V denotes C—R$^{31}$ and W denotes C—R$^{32}$ or T denotes N and U denotes C—R$^{30}$ and V denotes C—R$^{31}$ and W denotes C—R$^{32}$ or T denotes N and U denotes N and V denotes C—R$^{31}$ and W denotes C—R$^{32}$ or T denotes N and U denotes C—R$^{30}$ and V denotes N and W denotes C—R$^{32}$ or T denotes C—R$^{29}$ and U denotes N and V denotes N and W denotes C—R$^{32}$ or T denotes C—R$^{29}$ and U denotes C—R$^{30}$ and V denotes C—R$^{31}$ and W denotes C—R$^{32}$;

R$^9$ denotes F; Cl; Br; I; —SF$_5$; —OR$^{13}$; —SR$^{14}$; —S(=O)—R$^{23}$; —S(=O)$_2$—R$^{24}$;

denotes a residue selected from the group consisting of methyl, —CF$_3$, —CCl$_3$, —CBr$_3$, —CHF$_2$, —CH$_2$F, —CF$_2$Cl, —CCl$_2$F, —CH$_2$—CN, —CH$_2$—O—CH$_3$, —CH$_2$—O—CF$_3$, —CH$_2$—SF$_3$, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, —CH$_2$—CH$_2$—CN, n-propyl, —CF$_2$—CF$_2$—CF$_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SF$_3$, —CH$_2$—CH$_2$—OCF$_3$, —CH(CH$_3$)(O—CH$_3$), —CH(CH$_3$)(S—CH$_3$), n-butyl, —CF$_2$—CF$_2$—CF$_2$—CF$_3$, —CH$_2$—CH$_2$—CH$_2$—CH$_2$—CN, n-butyl, sec.-butyl, isobutyl, —C(CH$_3$)$_2$(CH$_2$OH) and tert.-butyl;

or denotes a residue selected from the group consisting of cyclopropyl, cyclobutyl, cyclopentyl, cyclohexyl, cycloheptyl, cyclopentenyl and cyclohexenyl, which may optionally in each case be substituted with 1, 2, 3, 4 or 5 substituents mutually independently selected from the group consisting of oxo (=O), thioxo (=S), —OH, —O—CH$_3$, —O—C$_2$H$_5$, —O—CH(CH$_3$)$_2$, —O—C(CH$_3$)$_3$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec.-butyl, isobutyl, tert.-butyl and n-pentyl;

R$^{10}$, R$^{11}$, R$^{12}$, R$^{13}$, R$^{14}$, R$^{21}$ and R$^{23}$ and R$^{24}$, mutually independently, in each case denote a residue selected from the group consisting of methyl, —CF$_3$, —CCl$_3$, —CBr$_3$, —CHF$_2$, —CH$_2$F, —CF$_2$Cl, —CCl$_2$F, —CH$_2$—CN, —CH$_2$—O—CH$_3$, —CH$_2$—O—CF$_3$, —CH$_2$—SF$_3$, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, —CH$_2$—CH$_2$—CN, n-propyl, —CF$_2$—CF$_2$—CF$_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SF$_3$, —CH$_2$—CH$_2$—OCF$_3$, —CH(CH$_3$)(O—CH$_3$), —CH(CH$_3$)(S—CH$_3$), n-butyl, —CF$_2$—CF$_2$—CF$_2$—CF$_3$, —CH$_2$—CH$_2$—CH$_2$—CH$_2$—CN, sec.-butyl, isobutyl, tert.-butyl, n-pentyl, 3-pentyl, n-heptyl, 4-heptyl, n-octyl, n-nonyl, 5-nonyl, (2,6)-dimethyl-hept-4-yl, 3-methylbutyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—CH$_2$—O—CH$_3$, ethenyl, propenyl, 2-butenyl, 3-butenyl, 2-pentenyl and 3-pentenyl;

denote a residue selected from the group consisting of 2,3-dihydro-1H-indenyl, cyclopropyl, oxetanyl, cyclobutyl, cyclopentyl, cyclohexyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, which may in each case be attached via a —CH$_2$—O—, —CH$_2$—CH$_2$—O—, —CH$_2$—CH$_2$—O—CH$_2$—, —CH$_2$—CH(CH$_3$)—O—CH$_2$—, —(CH$_2$)—, —(CH$_2$)$_2$— or —(CH$_2$)$_3$— group and/or in each case unsubstituted or optionally substituted with 1, 2, 3, 4 or 5 substituents mutually independently selected from the group consisting of oxo (=O), thioxo (=S), —OH, —O—CH$_3$, —O—C$_2$H$_5$, —O—CH(CH$_3$)$_2$, —O—C(CH$_3$)$_3$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec.-butyl, isobutyl, tert.-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$ and —C(=O)—O—C(CH$_3$)$_3$;

or denote a residue selected from the group consisting of phenyl, naphthyl, thiophenyl, furanyl, pyrrolyl, pyrazolyl, pyrazinyl, pyranyl, triazolyl, pyridinyl, imidazolyl, thiazolyl, oxazolyl and isoxazolyl, wherein the residue may in each case be attached via a —(CH$_2$)—, —(CH$_2$)$_2$— or —(CH$_2$)$_3$— group and/or may in each case be unsubstituted or optionally substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec.-butyl, isobutyl, tert.-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—NH$_2$, —C(=O)—NH—CH$_3$, —C(=O)—NH—C$_2$H$_5$, —C(=O)—N(CH$_3$)$_2$, —C(=O)—N(C$_2$H$_5$)$_2$, —O-phenyl, —O-benzyl, phenyl and benzyl;

R$^{25}$, R$^{26}$ and R$^{27}$, mutually independently, in each case denote an alkyl residue selected from the group consisting of —CF$_3$, —CH$_2$—CF$_3$, methyl, ethyl, n-propyl, isopropyl, tert.-butyl, n-butyl, sec.-butyl and isobutyl;

R$^{28}$ denotes a residue selected from the group consisting of methyl, —CF$_3$, —CCl$_3$, —CBr$_3$, —CHF$_2$, —CH$_2$F, —CF$_2$Cl, —CH$_2$—CN, —CH$_2$—O—CH$_3$, —CH$_2$—O—CF$_3$, —CH$_2$—SF$_3$, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, —CH$_2$—CH$_2$—CN, n-propyl, isopropyl, sec.-butyl, isobutyl, tert.-butyl, n-pentyl, 3-pentyl, n-heptyl, 4-heptyl, n-octyl, n-nonyl, 5-nonyl, (2,6)-dimethyl-hept-4-yl, 3-methylbutyl, n-hexyl, (3,3)-dimethylbutyl, ethenyl, propenyl, 2-butenyl, 3-butenyl, 2-pentenyl and 3-pentenyl;

R$^{29}$, R$^{30}$ and R$^{31}$, mutually independently, in each case denote H; F; Cl; Br; I; —SF$_5$; —NO$_2$; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{10}$; —NR$^{11}$R$^{12}$; —OR$^{13}$; —SR$^{14}$; —C(=O)—OR$^{21}$; —S(=O)—R$^{23}$; —S(=O)$_2$—R$^{24}$; denote a residue selected from the group consisting of —CH$_2$—OH, methyl, —CF$_3$, —CCl$_3$, —CBr$_3$, —CHF$_2$, —CH$_2$F, —CF$_2$Cl, —CCl$_2$F, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, n-propyl, —CF$_2$—CF$_2$—CF$_3$, —CF(CF$_3$)$_2$, isopropyl, n-butyl, sec.-butyl, isobutyl and tert.-butyl or denote a phenyl residue, which may be unsubstituted or optionally substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec.-butyl, isobutyl, tert.-butyl and n-pentyl;

R$^{32}$ denotes H; —SF$_5$; —NO$_2$; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{33}$; —NR$^{34}$R$^{35}$; —OR$^{36}$; —SR$^{37}$; —C(=O)—OR$^{44}$; —S(=O)—R$^{46}$; —S(=O)$_2$—R$^{47}$; —C(=NH)—NH$_2$; —C(=NH)—NH—R$^{48}$; —N=C(NH$_2$)$_2$; —N=C(NHR$^{49}$)(NHR$^{50}$);

denotes a residue selected from the group consisting of cyclopropyl, cyclobutyl, cyclopentyl, cyclohexyl, cyclohexenyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, which is in each case attached via a carbon atom of the rings of the above-stated residues or via a —(CH=CH)—, —C≡C— or —C≡C—CH$_2$— group to the parent structure and may be unsubstituted or optionally in each case substituted with 1, 2, 3, 4 or 5 substituents mutually independently selected from the group consisting of —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]-phenyl, —N—[C(=O)—CH$_3$]-phenyl, oxo (=O), thioxo (=S), —OH, —O—CH$_3$, —O—C$_2$H$_5$, —O—CH(CH$_3$)$_2$, —O—C(CH$_3$)$_3$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec.-butyl, isobutyl, tert.-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$ and —C(=O)—O—C(CH$_3$)$_3$;

or denotes a residue selected from the group consisting of (1,3)-benzodioxolyl, (1,4)-benzodioxanyl, tetrazolyl, (2,3)-dihydrothieno[3,4-b][1,4]dioxinyl, benzo[b]furanyl, phenyl, naphthyl, thiophenyl, furanyl, pyrrolyl, pyrazolyl, pyrazinyl, pyranyl, triazolyl, pyridinyl, imidazolyl, indolyl, isoindolyl, thiazolyl, oxazolyl, isoxazolyl, pyridazinyl, pyrazinyl, pyrimidinyl, indazolyl, quinoxalinyl, quinolinyl and isoquinolinyl, which may in each case be attached via a —(CH=CH)—, —C≡C—, —(CH$_2$)—, —(CH$_2$)$_2$— or —(CH$_2$)$_3$— group and/or may in each case be unsubstituted or optionally substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec.-butyl, isobutyl, tert.-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH—C(=O)—O—CH$_3$, —NH—S(=O)$_2$—CH$_3$, —NH—S(=O$_2$)—C$_2$H$_5$, —NH—S(=O)$_2$—CH(CH$_3$)$_2$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—NH$_2$, —C(=O)—NH—CH$_3$, —C(=O)—NH—C$_2$H$_5$, —C(=O)—N(CH$_3$)$_2$, —C(=O)—N(C$_2$H$_5$)$_2$, —O-phenyl, —O-benzyl, phenyl and benzyl;

R$^{33}$, R$^{34}$, R$^{35}$, R$^{36}$, R$^{37}$, R$^{44}$, R$^{46}$, R$^{47}$, R$^{48}$, R$^{49}$ and R$^{50}$, mutually independently, in each case denote a residue selected from the group consisting of methyl, —CF$_3$, —CCl$_3$, —CBr$_3$, —CHF$_2$, —CH$_2$F, —CF$_2$Cl, —CCl$_2$F, —CH$_2$—CN, —CH$_2$—O—CH$_3$, —CH$_2$—O—CF$_3$, —CH$_2$—SF$_3$, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, —CH$_2$—CH$_2$—CN, n-propyl, —CF$_2$—CF$_2$—CF$_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SF$_3$, —CH$_2$—CH$_2$—OCF$_3$, —CH(CH$_3$)(O—CH$_3$), —CH(CH$_3$)(S—CH$_3$), n-butyl, —CF$_2$—CF$_2$—CF$_2$—CF$_3$, —CH$_2$—CH$_2$—CH$_2$—CH$_2$—CN, sec.-butyl, isobutyl, tert.-butyl, n-pentyl, 3-pentyl, n-heptyl, 4-heptyl, n-octyl, n-nonyl, 5-nonyl, (2,6)-dimethyl-hept-4-yl, 3-methylbutyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—CH$_2$—O—CH$_3$, ethenyl, propenyl, 2-butenyl, 3-butenyl, 2-pentenyl and 3-pentenyl;

denote a residue selected from the group consisting of 2,3-dihydro-1H-indenyl, cyclopropyl, oxetanyl, cyclobutyl, cyclopentyl, cyclohexyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, which may in each case be attached via a —CH$_2$—O—, —CH$_2$—CH$_2$—O—, —CH$_2$—CH$_2$—O—CH$_2$—, —CH$_2$—CH(CH$_3$)—O—CH$_2$—, —(CH$_2$)—, —(CH$_2$)$_2$— or —(CH$_2$)$_3$— group and/or may in each case be unsubstituted or optionally substituted with 1, 2, 3, 4 or 5 substituents mutually independently selected from the group consisting of oxo (=O), thioxo (=S), —OH, —O—CH$_3$, —O—C$_2$H$_5$, —O—CH(CH$_3$)$_2$, —O—C(CH$_3$)$_3$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec.-butyl, isobutyl, tert.-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$ and —C(=O)—O—C(CH$_3$)$_3$;

or denote a residue selected from the group consisting of phenyl, naphthyl, thiophenyl, furanyl, pyrrolyl, pyrazolyl, pyrazinyl, pyranyl, triazolyl, pyridinyl, imidazolyl, thiazolyl, oxazolyl and isoxazolyl, wherein the residue may in each case be attached via a —(CH$_2$)—, —(CH$_2$)$_2$— or —(CH$_2$)$_3$— group and/or may in each case be unsubstituted or optionally be substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec.-butyl, isobutyl, tert.-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—NH$_2$, —C(=O)—NH—CH$_3$, —C(=O)—NH—C$_2$H$_5$, —C(=O)—N(CH$_3$)$_2$, —C(=O)—N(C$_2$H$_5$)$_2$, —O-phenyl, —O-benzyl, phenyl and benzyl;

or

R$^{34}$ and R$^{35}$ in each case together with the nitrogen atom joining them together as a ring member form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, piperazinyl, morpholinyl, azepanyl, diazepanyl and thiomorpholinyl, the heterocycloaliphatic moiety of which may in each case be unsubstituted or substituted with 1, 2, 3, 4 or 5 residues R$^{51}$;

R$^{51}$ denotes —NHR$^{52}$, —NR$^{53}$R$^{54}$ or denotes an alkyl residue selected from the group consisting of —CF$_3$, —CH$_2$—CF$_3$, methyl, ethyl, n-propyl, isopropyl, tert.-butyl, n-butyl, sec.-butyl and isobutyl;

R$^{52}$, R$^{53}$ and R$^{54}$, mutually independently, in each case denote-C(=O)—R$^{55}$;

denote an alkyl residue selected from the group consisting of —CF$_3$, —CH$_2$—CF$_3$, methyl, ethyl, n-propyl, isopropyl, tert.-butyl, n-butyl, sec.-butyl, and isobutyl;

or denote a residue selected from the group consisting of phenyl, naphthyl, thiophenyl, furanyl, pyrrolyl, pyrazolyl, pyrazinyl, pyranyl, triazolyl, pyridinyl, imidazolyl, thiazolyl, oxazolyl and isoxazolyl, wherein the residue may in each case be attached via a —(CH$_2$)—, —(CH$_2$)$_2$— or —(CH$_2$)$_3$— group and/or may in each case be unsubstituted or optionally substituted with 1, 2, 3, 4 or 5 substituents mutually independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec.-butyl, isobutyl, tert.-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)(C$_2$H$_5$), —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—NH$_2$, —C(=O)—NH—CH$_3$, —C(=O)—NH—C$_2$H$_5$, —C(=O)—N(CH$_3$)$_2$, —C(=O)—N(C$_2$H$_5$)$_2$, —O-phenyl, —O-benzyl, phenyl and benzyl;

and

R$^{55}$ denotes an alkyl residue selected from the group consisting of —CF$_3$, —CH$_2$—CF$_3$, methyl, ethyl, n-propyl, isopropyl, tert.-butyl, n-butyl, sec.-butyl and isobutyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particularly preferred compounds are those of the general formula Ia,

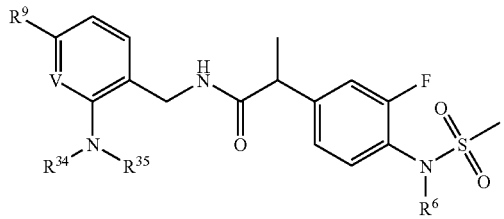

in which

V denotes N or CH;

R$^6$ denotes —C(=O)—R$^{28}$ or denotes a residue selected from the group consisting of methyl, —CH$_2$—CN, ethyl, —CH$_2$—CH$_2$—CN, n-propyl, —CH$_2$—CH$_2$—CH$_2$—CN, n-butyl, —CH$_2$—CH$_2$—CH$_2$—CH$_2$—CN, sec.-butyl, isobutyl, tert.-butyl, n-pentyl, 3-pentyl, n-heptyl, ethenyl, propenyl, 2-butenyl, 3-butenyl, 2-pentenyl and 3-pentenyl;

R$^9$ denotes F; Cl; Br; I; —SF$_5$; —O—CF$_3$; —O—CCl$_3$; —O—CBr$_3$; —O—CHF$_2$; —O—CH$_2$F; —O—CF$_2$Cl; —O—CCl$_2$F; —O—CF$_2$—CH$_3$; —S—CF$_3$; —S—CCl$_3$; —S—CBr$_3$; —S—CHF$_2$; —S—CH$_2$F; —S—CF$_2$Cl; —S—CCl$_2$F; —S—CF$_2$—CH$_3$; or denotes a residue selected from the group consisting of methyl, —CF$_3$, —CHF$_2$, —CH$_2$F, ethyl, n-propyl, isopropyl, n-butyl, sec.-butyl, isobutyl, —C(CH$_3$)$_2$(CH$_2$OH) and tert.-butyl;

R$^{28}$ denotes a residue selected from the group consisting of methyl, ethyl, n-propyl, isopropyl, sec.-butyl, isobutyl, tert.-butyl, n-pentyl, 3-pentyl, n-heptyl, 4-heptyl, n-octyl, n-nonyl, 5-nonyl, (2,6)-dimethyl-hept-4-yl, 3-methylbutyl, n-hexyl, (3,3)-dimethylbutyl, ethenyl, propenyl, 2-butenyl, 3-butenyl, 2-pentenyl and 3-pentenyl;

$R^{34}$ and $R^{35}$, mutually independently, in each case
  denote a residue selected from the group consisting of methyl, —$CH_2$—O—$CH_3$, ethyl, n-propyl, n-butyl, sec.-butyl, isobutyl, tert.-butyl, n-pentyl, 3-pentyl, n-hexyl, (3,3)-dimethylbutyl, —$CH_2$—$CH_2$—O—$CH_3$, —$CH_2$—$CH_2$—O—$C_2H_5$ and —$CH_2$—$CH_2$—$CH_2$—O—$CH_3$;
  denote a residue selected from the group consisting of 2,3-dihydro-1H-indenyl, cyclopropyl, oxetanyl, cyclobutyl, cyclopentyl, cyclohexyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, which may in each case optionally be substituted with 1, 2, 3, 4 or 5 substituents mutually independently selected from the group consisting of methyl, ethyl, n-propyl, isopropyl, n-butyl, sec.-butyl, isobutyl, tert.-butyl, n-pentyl;

or $R^{34}$ and $R^{35}$ in each case together with the nitrogen atom joining them together as a ring member form a residue selected from the group consisting of 3-aza-bicyclo[3.1.1]heptyl, 6-aza-spiro[2.5]octyl, 3-aza-bicyclo[3.2.1]octyl, 6-aza-bicyclo[3.3.1]heptyl, 8-aza-bicyclo[3.2.1]octyl, 1-oxa-2,8-diaza-spiro[4.5]dec-2-enyl, azocanyl, isoindolyl, indolyl, (1,2,3,6)-tetrahydropyridinyl, (4,5,6,7)-tetrahydroisoxazolo[5,4-c]pyridinyl, pyrrolidinyl, piperidinyl, piperazinyl, morpholinyl, azepanyl, diazepanyl and thiomorpholinyl, the heterocycloaliphatic moiety of which may in each case be unsubstituted or substituted with 1, 2, 3, 4 or 5 residues $R^{51}$;

$R^{51}$ denotes —$NHR^{52}$, —$NR^{53}R^{54}$ or denotes an alkyl residue selected from the group consisting of —$CF_3$, —$CH_2$—$CF_3$, methyl, ethyl, n-propyl, isopropyl, tert.-butyl, n-butyl, sec.-butyl and isobutyl;

$R^{52}$, $R^{53}$ and $R^{54}$, mutually independently, in each case denote-C(=O)—$R^{55}$;
  denote an alkyl residue selected from the group consisting of —$CF_3$, —$CH_2$—$CF_3$, methyl, ethyl, n-propyl, isopropyl, tert.-butyl, n-butyl, sec.-butyl, and isobutyl;
  or denote a residue selected from the group consisting of phenyl and naphthyl, wherein the residue may in each case be attached via a —($CH_2$)—, —($CH_2$)$_2$— or —($CH_2$)$_3$— group and/or in each case unsubstituted or optionally substituted with 1, 2, 3, 4 or 5 substituents mutually independently selected from the group consisting of F, Cl, Br, I, —CN, —$CF_3$, —O—$CH_3$, —O—$C_2H_5$, —O—CH($CH_3$)$_2$, —O—C($CH_3$)$_3$, methyl, ethyl, n-propyl, isopropyl, n-butyl, sec.-butyl, isobutyl, tert.-butyl and n-pentyl;

and $R^{55}$ denotes an alkyl residue selected from the group consisting of —$CF_3$, —$CH_2$—$CF_3$, methyl, ethyl, n-propyl, isopropyl, tert.-butyl, n-butyl, sec.-butyl and isobutyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particularly preferred compounds are those of the above-stated general formula Ia, in which, $R^6$ denotes —C(=O)—$R^{28}$ or denotes a residue selected from the group consisting of methyl, —$CH_2$—CN, ethyl, —$CH_2$—$CH_2$—CN, n-propyl, —$CH_2$—$CH_2$—$CH_2$—CN, n-butyl, —$CH_2$—$CH_2$—$CH_2$—$CH_2$—CN, sec.-butyl, isobutyl, tert.-butyl and n-pentyl;

$R^9$ denotes —$SF_5$; —O—$CF_3$; —$CF_3$; —$CHF_2$; —$CH_2F$; —C($CH_3$)$_2$($CH_2OH$) or tert.-butyl;

$R^{28}$ denotes a residue selected from the group consisting of methyl, ethyl, n-propyl, isopropyl, sec.-butyl, isobutyl, tert.-butyl, ethenyl and propenyl;

$R^{34}$ and $R^{35}$ in each case together with the nitrogen atom joining them together as a ring member form a residue selected from the group consisting of pyrrolidinyl, piperidinyl, piperazinyl, morpholinyl and azepanyl, the heterocycloaliphatic moiety of which may in each case be unsubstituted or substituted with 1, 2, 3, 4 or 5 residues $R^{51}$;

$R^{51}$ denotes —$NHR^{52}$, —$NR^{53}R^{54}$ or denotes an alkyl residue selected from the group consisting of methyl, ethyl, n-propyl, isopropyl, tert.-butyl, n-butyl, sec.-butyl and isobutyl;

$R^{52}$, $R^{53}$ and $R^{54}$, mutually independently, in each case denote-C(=O)—$R^{55}$;
  denote an alkyl residue selected from the group consisting of methyl, ethyl, n-propyl, isopropyl, tert.-butyl, n-butyl, sec.-butyl, and isobutyl;
  or denote a phenyl residue, wherein the residue may be substituted with 1, 2, 3, 4 or 5 substituents mutually independently selected from the group consisting of F, Cl, Br, methyl, ethyl, n-propyl and isopropyl;
and $R^{55}$ denotes an alkyl residue selected from the group consisting of methyl, ethyl, n-propyl, isopropyl, tert.-butyl, n-butyl, sec.-butyl, and isobutyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Particularly preferred compounds are those of the general formula Ib,

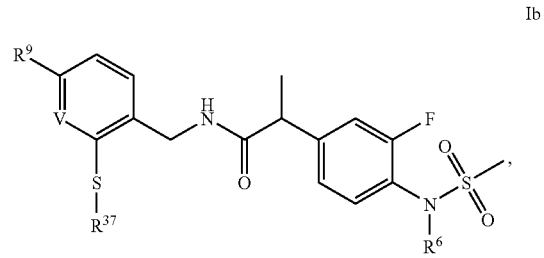

Ib in which $R^6$ denotes —C(=O)—$R^{28}$ or denotes a residue selected from the group consisting of methyl, —$CH_2$—CN, ethyl, —$CH_2$—$CH_2$—CN, n-propyl, —$CH_2$—$CH_2$—$CH_2$—CN, n-butyl, —$CH_2$—$CH_2$—$CH_2$—$CH_2$—CN, sec.-butyl, isobutyl, tert.-butyl, n-pentyl, 3-pentyl, n-heptyl, ethenyl, propenyl, 2-butenyl, 3-butenyl, 2-pentenyl and 3-pentenyl;

$R^9$ denotes F; Cl; Br; I; —$SF_5$; —O—$CF_3$; —O—$CCl_3$; —O—$CBr_3$; —O—$CHF_2$; —O—$CH_2F$; —O—$CF_2Cl$; —O—$CCl_2F$; —O—$CF_2$—$CH_3$; —S—$CF_3$; —S—$CCl_3$; —S—$CBr_3$; —S—$CHF_2$; —S—$CH_2F$; —S—$CF_2Cl$; —S—$CCl_2F$; —S—$CF_2$—$CH_3$; or denotes a residue selected from the group consisting of methyl, —$CF_3$, —$CHF_2$, —$CH_2F$, ethyl, n-propyl, isopropyl, n-butyl, sec.-butyl, isobutyl, —C($CH_3$)$_2$($CH_2OH$) and tert.-butyl;

$R^{28}$ denotes a residue selected from the group consisting of methyl, ethyl, n-propyl, isopropyl, sec.-butyl, isobutyl, tert.-butyl, n-pentyl, 3-pentyl, n-heptyl, 4-heptyl, n-octyl, n-nonyl, 5-nonyl, (2,6)-dimethyl-hept-4-yl, 3-methylbutyl, n-hexyl, (3,3)-dimethylbutyl, ethenyl, propenyl, 2-butenyl, 3-butenyl, 2-pentenyl and 3-pentenyl;

and $R^{37}$ denotes a residue selected from the group consisting of methyl, —CH$_2$—O—CH$_3$, ethyl, n-propyl, n-butyl, sec.-butyl, isobutyl, tert.-butyl, n-pentyl, 3-pentyl, n-hexyl, (3,3)-dimethylbutyl, —CH$_2$—CH$_2$—O—CH$_3$, —CH$_2$—CH$_2$—O—C$_2$H$_5$ and —CH$_2$—CH$_2$—CH$_2$—O—CH$_3$;

or denotes a residue selected from the group consisting of 2,3-dihydro-1H-indenyl, cyclopropyl, oxetanyl, cyclobutyl, cyclopentyl, cyclohexyl, imidazolidinyl, tetrahydrofuranyl, tetrahydrothiophenyl, pyrrolidinyl, piperidinyl, morpholinyl, piperazinyl, azepanyl, diazepanyl, azocanyl and thiomorpholinyl, which may in each case optionally be substituted with 1, 2, 3, 4 or 5 substituents mutually independently selected from the group consisting of methyl, ethyl, n-propyl, isopropyl, n-butyl, sec.-butyl, isobutyl, tert.-butyl, n-pentyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Very particularly preferred compounds are those of the above-stated general formula Ib, in which $R^6$ denotes —C(=O)—$R^{28}$ or denotes a residue selected from the group consisting of methyl, —CH$_2$—CN, ethyl, —CH$_2$—CH$_2$—CN, n-propyl, —CH$_2$—CH$_2$—CH$_2$—CN, n-butyl, —CH$_2$—CH$_2$—CH$_2$—CH$_2$—CN, sec.-butyl, isobutyl, tert.-butyl and n-pentyl;

$R^9$ denotes —SF$_5$; —O—CF$_3$; —CF$_3$; —CHF$_2$; —CH$_2$F; —C(CH$_3$)$_2$(CH$_2$OH) or tert.-butyl;

$R^{28}$ denotes a residue selected from the group consisting of methyl, ethyl, n-propyl, isopropyl, sec.-butyl, isobutyl, tert.-butyl, ethenyl and propenyl;

and $R^{37}$ denotes a residue selected from the group consisting of cyclopropyl, cyclobutyl, cyclopentyl, cyclohexyl and cycloheptyl, which may in each case optionally be substituted with 1, 2, 3, 4 or 5 substituents mutually independently selected from the group consisting of methyl, ethyl, n-propyl, isopropyl, n-butyl, sec.-butyl, isobutyl, tert.-butyl, n-pentyl;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

The present invention further preferably provides compounds of the general formula I', I" and I'".

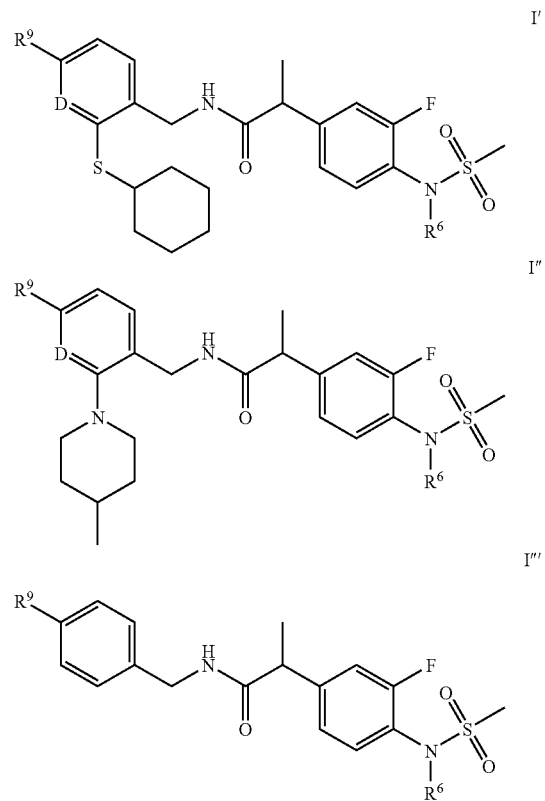

in which in each case
D denotes N or CH
$R^9$ denotes CF$_3$ or denotes tert.-butyl
$R^6$ denotes methyl, ethyl, —C(=O)—CH$_3$ or —C(=O)—CH$_2$CH$_3$, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Still more preferred are compounds of the general formulae I, Ia, Ib, I', I" and I'" selected from the group consisting of

[1] N-(2-fluoro-4-(1-oxo-1-((2-(4-(N-phenylpropionamido)piperidin-1-yl)-6-(trifluoromethyl)pyridin-3-yl)methylamino)propan-2-yl)phenyl)-N-(methylsulfonyl)propionamide,

[2] 2-(3-fluoro-4-(N-(methylsulfonyl)acetamido)phenyl)-N-((2-(4-methylpiperidin-1-yl)-6-(trifluoromethyl)pyridin-3-yl)methyl)propanamide,

[3] 2-(3-fluoro-4-(N-methylmethylsulfonamido)phenyl)-N-((2-(4-methylpiperidin-1-yl)-6-(trifluoromethyl)pyridin-3-yl)methyl)propanamide,

[4] N-(4-tert.-butylbenzyl)-2-(3-fluoro-4-(N-methylmethylsulfonamido)phenyl)propanamide,

[5] (S)—N-(4-tert.-butylbenzyl)-2-(3-fluoro-4-(N-methylethylsulfonamido)phenyl)propanamide,

[6] (S)—N-(4-tert.-butylbenzyl)-2-(4-(N-ethylmethylsulfonamido)-3-fluorophenyl)propanamide,

[7] N-((2-(cyclohexylthio)-6-(trifluoromethyl)pyridin-3-yl)methyl)-2-(3-fluoro-4-(N-methylmethylsulfonamido)phenyl)propanamide,

[8] N-((2-(cyclohexylthio)-6-(trifluoromethyl)pyridin-3-yl)methyl)-2-(4-(N-ethylmethylsulfonamido)-3-fluorophenyl)propanamide,
[9] 2-(4-(N-ethylmethylsulfonamido)-3-fluorophenyl)-N-((2-(4-methylpiperidin-1-yl)-6-(trifluoromethyl)pyridin-3-yl)methyl)propanamide,
[10] N-((6-tert.-butyl-2-(4-methylpiperidin-1-yl)pyridin-3-yl)methyl)-2-(3-fluoro-4-(N-methylmethylsulfonamido)phenyl)propanamide,
[11] N-((6-tert.-butyl-2-(cyclohexylthio)pyridin-3-yl)methyl)-2-(3-fluoro-4-(N-methylmethylsulfonamido)phenyl)propanamide,
[12] 2-(3-fluoro-4-(N-methylmethylsulfonamido)phenyl)-N-(2-(4-methylpiperidin-1-yl)-4-(trifluoromethyl)benzyl)propanamide,
[13] N-(2-(cyclohexylthio)-4-(trifluoromethyl)benzyl)-2-(3-fluoro-4-(N-methylmethylsulfonamido)phenyl)propanamide,
[14] N-(4-tert.-butyl-2-(4-methylpiperidin-1-yl)benzyl)-2-(3-fluoro-4-(N-methylmethylsulfonamido)phenyl)propanamide and
[15] N-(4-tert.-butyl-2-(cyclohexylthio)benzyl)-2-(3-fluoro-4-(N-methylmethylsulfonamido)phenyl)propanamide, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

In addition, compounds according to the invention of the general formulae I, Ia, Ib, I', I'', I''' may be preferred which, in a FLIPR assay with CHO K1 cells which have been transfected with the human gene VR1, in a concentration of less than 2000 nM, preferably of less than 1000 nM, particularly preferably of less then 300 nM, very particularly preferably of less than 100 nM, still more preferably of less than 75 nM, further preferably of less than 50 nM, most preferably of less than 10 nM, bring about 50% displacement of capsaicin which is present in a concentration of 100 nM.

In this FLIPR assay, the influx of $Ca^{2+}$ is quantified with the assistance of a $Ca^{2+}$-sensitive dye (type Fluo-4, Molecular Probes Europe BV, Leiden, Netherlands) in a Fluorescent Imaging Plate Reader (FLIPR, Molecular Devices, Sunnyvale, USA) as described below.

The present invention also provides a method for the production of compounds of the above-stated general formulae I, Ia, Ib, I', I'', I''' in accordance with which at least one compound of the general formula II,

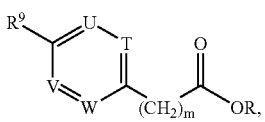

in which $R^9$, U, T, V, and W have the above-stated meanings, m denotes 0, 1, 2 or 3 and R denotes hydrogen or denotes a linear or branched $C_{1-6}$ alkyl residue, is reacted in a reaction medium, in the presence of at least one reducing agent, preferably in the presence of at least one reducing agent selected from the group consisting of sodium hydride, sodium, potassium hydride, lithium aluminium hydride, sodium borohydride and di(isobutyl)aluminium hydride to yield at least one compound of the general formula III,

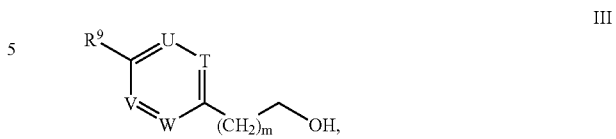

in which $R^9$, U, T, V and W have the above-stated meanings and m denotes 0, 1, 2 or 3 and said compound is optionally purified and/or isolated, and at least one compound of the general formula III is reacted in a reaction medium in the presence of diphenylphosphoryl azide or in the presence of $HN_3$ to yield at least one compound of the general formula IV,

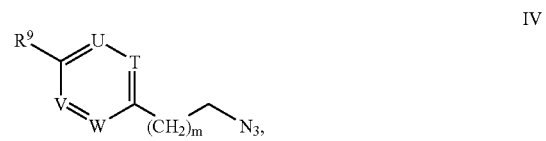

in which $R^9$, U, T, V and W have the above-stated meanings and m denotes 0, 1, 2 or 3 and said compound is optionally purified and/or isolated, and at least one compound of the general formula IV is reacted in a reaction medium in the presence of at least one reducing agent, preferably in the presence of at least one reducing agent selected from the group consisting of sodium hydride, potassium hydride, lithium aluminium hydride, sodium borohydride and di(isobutyl)aluminium hydride or in a reaction medium in the presence of a catalyst, preferably in the presence of a catalyst based on platinum or palladium, particularly preferably in the presence of palladium on carbon, and in the presence of hydrogen or in the presence of hydrazine or in a reaction medium in the presence of triphenylphosphine to yield at least one compound of the general formula V,

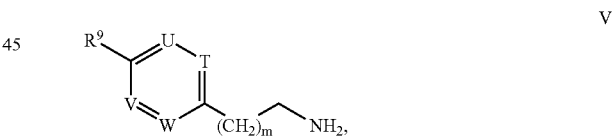

in which $R^9$, U, T, V and W have the above-stated meanings and m denotes 0, 1, 2 or 3 and said compound is optionally purified and/or isolated, or at least one compound of the general formula VI,

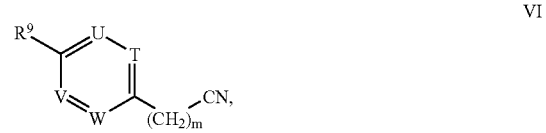

in which $R^9$, U, T, V, and W have the above-stated meanings and m denotes 0, 1, 2 or 3, is reacted in a reaction medium in the presence of at least one catalyst, preferably in the presence of at least one catalyst based on palladium or platinum, particularly preferably in the presence of palladium on carbon, under a hydrogen atmosphere, optionally in the presence of at least one acid, preferably in the presence of hydrochloric acid,
or in the presence of at least one reducing agent selected from the group consisting of $BH_3 \cdot S(CH_3)_2$, lithium aluminium hydride and sodium borohydride, optionally in the presence of $NiCl_2$,
to yield at least one compound of the general formula V, optionally in the form of a corresponding salt, preferably in the form of a corresponding hydrochloride, and said compound is optionally purified and/or isolated,
and at least one compound of the general formula V is reacted with at least one compound of the general formula VII,

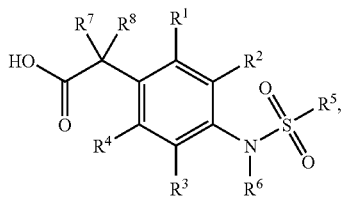

VII in which $R^1$, $R^2$, $R^3$, $R^4$, $R^5$, $R^6$, $R^7$ and $R^8$ have the above-stated meanings and $R^6$ may additionally denote a hydrogen residue, in a reaction medium, optionally in the presence of at least one suitable coupling agent, optionally in the presence of at least one base,
or with at least one compound of the general formula VIII,

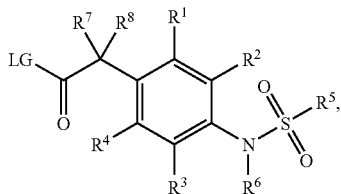

VIII in which $R^1$, $R^2$, $R^3$, $R^4$, $R^5$, $R^6$, $R^7$ and $R^8$ have the above-stated meanings, $R^6$ may additionally denote a hydrogen residue and LG denotes a leaving group, preferably denotes a chlorine or bromine atom, in a reaction medium, optionally in the presence of at least one base, to yield at least one compound of the general formula Ih,

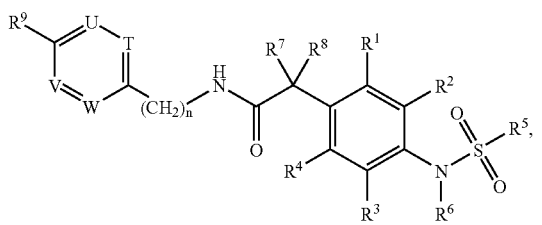

Ih in which T, U, V, W, $R^1$, $R^2$, $R^3$, $R^4$, $R^5$, $R^6$, $R^7$, $R^8$ and $R^9$, have the above-stated meanings, $R^6$ may additionally denote a hydrogen residue and n denotes 1, 2, 3 or 4, and said compound is optionally purified and/or isolated,
and optionally at least one compound of the general formula Ih is reacted in a reaction medium with at least one compound of the general formula IX,

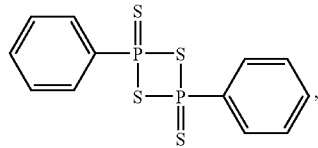

IX in which the phenyl residues are in each case substituted with 1 or 2 substituents mutually independently selected from the group consisting of methoxy, phenoxy, Cl, methyl and Br, preferably in each case with a phenoxy residue or methoxy residue, particularly preferably in each case with a methoxy residue in para position, or with phosphorus pentasulfide, to yield at least one compound of the general formula Ik,

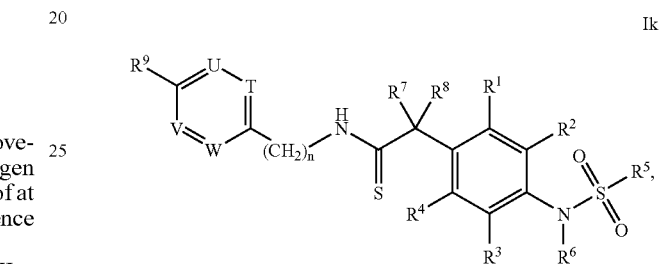

Ik in which T, U, V, W, $R^1$, $R^2$, $R^3$, $R^4$, $R^5$, $R^6$, $R^7$, $R^8$ and $R^9$ have the above-stated meanings, $R^6$ may additionally denote a hydrogen residue and n denotes 1, 2, 3 or 4, and said compound it optionally purified and/or isolated;

and optionally at least one compound of the general formula Io,

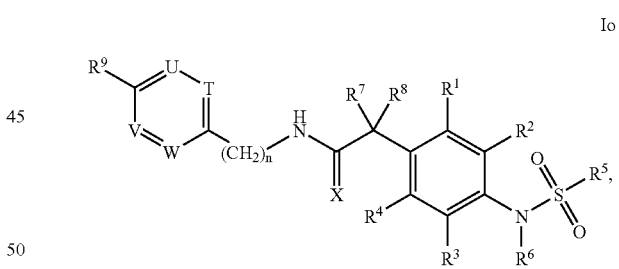

Io in which X, T, U, V, W, $R^1$, $R^2$, $R^3$, $R^4$, $R^5$, $R^7$, $R^8$ and $R^9$ have the above-stated meanings, $R^6$ denotes a hydrogen residue and n denotes 1, 2, 3 or 4, is reacted in a reaction medium in the presence of at least one compound of the general formula $R^{28}$—C(=O)—O—C(=O)—$R^{28}$, in which $R^{28}$ has the above-stated meaning, to yield at least one compound of the general formula I, in which X, T, U, V, W, $R^1$, $R^2$, $R^3$, $R^4$, $R^5$, $R^7$, $R^8$ and $R^9$ have the above-stated meanings, $R^6$ denotes —C(=O)—$R^{28}$ and n denotes 1, 2, 3 or 4, and said compound is optionally purified and/or isolated.

The present invention also provides a method for producing compounds of the above-stated general formulae I, Ia, Ib, I', I'' and I''', in accordance with which at least one compound of the general formula X,

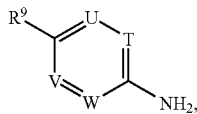

in which $R^9$, U, T, V, and W have the above-stated meanings, is reacted with at least one compound of the general formula VIII,

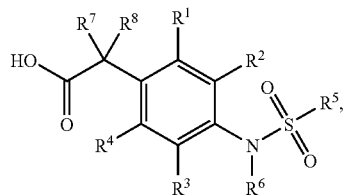

in which $R^1$, $R^2$, $R^3$, $R^4$, $R^5$, $R^6$, $R^7$ and $R^8$ have the above-stated meanings and $R^6$ may additionally denote a hydrogen residue, in a reaction medium, optionally in the presence of at least one suitable coupling agent, optionally in the presence of at least one base, or with at least one compound of the general formula VIII,

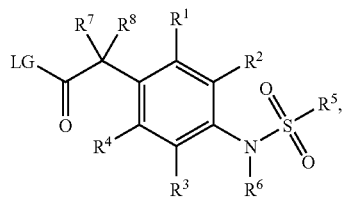

in which $R^1$, $R^2$, $R^3$, $R^4$, $R^5$, $R^6$, $R^7$ and $R^8$ have the above-stated meanings, $R^6$ may additionally denote a hydrogen residue and LG denotes a leaving group, preferably for a chlorine or bromine atom, in a reaction medium, optionally in the presence of at least one base, to yield at least one compound of the general formula Im,

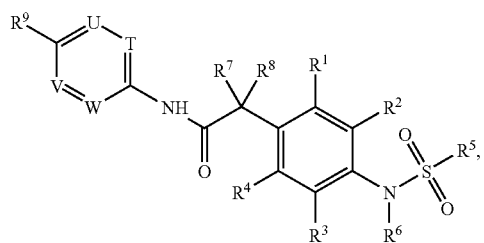

in which T, U, V, W, $R^1$, $R^2$, $R^3$, $R^4$, $R^5$, $R^7$, $R^8$ and $R^9$ have the above-stated meanings, and said compound is optionally purified and/or isolated, and optionally at least one compound of the general formula Im is reacted in a reaction medium with at least one compound of the general formula IX,

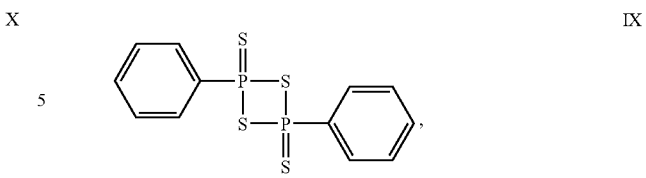

in which the phenyl residues are in each case substituted with 1 or 2 substituents mutually independently selected from the group consisting of methoxy, phenoxy, Cl, methyl and Br, preferably in each case with a phenoxy residue or methoxy residue, particularly preferably in each case with a methoxy residue in para position, or with phosphorus pentasulfide, to yield at least one compound of the general formula In,

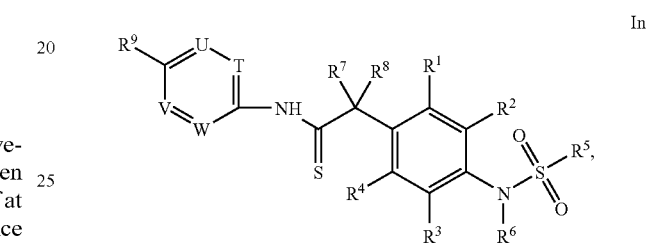

in which T, U, V, W, $R^1$, $R^2$, $R^3$, $R^4$, $R^5$, $R^6$, $R^7$, $R^8$ and $R^9$ have the above-stated meanings and $R^6$ may additionally denote a hydrogen residue, and said compound is optionally purified and/or isolated;

and optionally at least one compound of the general formula Ip,

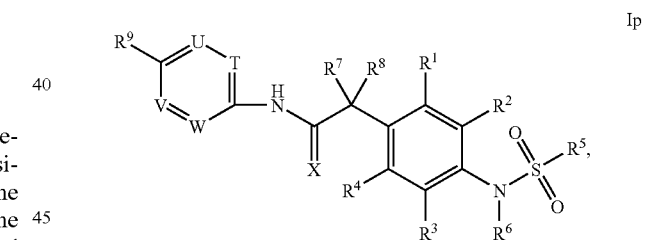

in which X, T, U, V, W, $R^1$, $R^2$, $R^3$, $R^4$, $R^5$, $R^7$, $R^8$ and $R^9$ have the above-stated meanings and $R^6$ denotes a hydrogen residue, is reacted in a reaction medium in the presence of at least one compound of the general formula $R^{28}$—C(=O)—O—C(=O)—$R^{28}$, in which $R^{28}$ has the above-stated meaning, to yield at least one compound of the general formula I, in which X, T, U, V, W, $R^1$, $R^2$, $R^3$, $R^4$, $R^5$, $R^7$, $R^8$ and $R^9$ have the above-stated meanings and $R^6$ denotes —C(=O)—$R^{28}$, and said compound is optionally purified and/or isolated.

The reaction of compounds of the above-stated general formulae V or X with carboxylic acids of the above-stated general formula VII to yield compounds of the above-stated general formulae Ih or Im proceeds preferably in a reaction medium selected from the group consisting of diethyl ether, tetrahydrofuran, acetonitrile, methanol, ethanol, (1,2)-dichloroethane, dimethylformamide, dichloromethane and corresponding mixtures, optionally in the presence of at least one coupling reagent, preferably selected from the group consisting of 1-benzotriazolyloxy-tris-(dimethylamino)-phosphonium hexafluorophosphate (BOP), dicyclohexylcarbodiimide (DCC), N'-(3-dimethylaminopropyl)-N-ethylcarbodiimide (EDCI), diisopropylcarbodiimide, 1,1'-carbonyldiimidazole (CDI), N-(dimethylamino)-1H-1,2,3-triazolo[4,5-b]pyridino-1-ylmethylene]-N-methylmethanaminium hexafluorophosphate N-oxide (HATU), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU) and 1-hydroxy-7-azabenzotriazole (HOAt), optionally in the presence of at least one organic base, preferably selected from the group consisting of triethylamine, pyridine, dimethylaminopyridine, N-methylmorpholine and diisopropylethylamine, preferably at temperatures of −70° C. to 100° C.

Alternatively, the reaction of compounds of the above-stated general formulae V or X with carboxylic acid derivatives of the above-stated general formula VIII, in which LG denotes a leaving group, preferably a chlorine or bromine atom, to yield compounds of the above-stated general formulae Ih or Im proceeds in a reaction medium preferably selected from the group consisting of diethyl ether, tetrahydrofuran, acetonitrile, methanol, ethanol, dimethylformamide, dichloromethane and corresponding mixtures, optionally in the presence of an organic base or inorganic base, preferably selected from the group consisting of triethylamine, dimethylaminopyridine, pyridine and diisopropylamine, at temperatures of −70° C. to 100° C.

The reaction of compounds of the general formulae Ih or Im to yield compounds of the general formulae Ik or In preferably proceeds in a reaction medium selected from the group consisting of toluene, para-xylene, ortho-xylene, meta-xylene, acetonitrile, dichloromethane, dimethylformamide and mixtures of the above-stated reaction media, with the addition of a dithiaphosphetane, particularly preferably with the addition of 2,4-bis(4-methoxyphenyl)-1,3,2,4-dithiadiphosphetane-2,4-disulfide (Lawesson's reagent), or with the addition of phosphorus pentasulfide, at temperatures of 50 to 150° C.

The compounds of the above-stated formulae II, III, IV, V, VI, VIII, IX and X are in each case commercially obtainable and may also be produced using conventional methods known to a person skilled in the art.

The synthesis method for compounds of the general formula VII may be found in the document "4-(Methylsulfonylamino)phenyl analogues as vanilloid antagonist showing excellent analgesic activity and the pharmaceutical compositions comprising the same" by J. W. Lee et al. [WO 2005/003084-A1]. The corresponding parts of the reference are hereby deemed to be part of the disclosure.

The above-described reactions may in each case be performed under conventional conditions familiar to a person skilled in the art, for example with regard to pressure or the sequence of addition of the components. Optimum control of the process under the respective conditions may optionally be established by the person skilled in the art by simple preliminary testing. The intermediate and final products obtained from the above-described reactions may in each case, if desired and/or necessary, be purified and/or isolated using conventional methods known to a person skilled in the art. Suitable purification methods are, for example, extraction methods and chromatographic methods such as column chromatography or preparative chromatography. All the above-described method steps and in each case also the purification and/or isolation of intermediate or final products may be performed in part or entirely under an inert gas atmosphere, preferably under a nitrogen atmosphere.

Preferred compounds of the general formulae I, Ia, Ib, 1', I''' and I''' may in each case be present as an (S)-enantiomer. For example, the (S)-enantiomer of compounds of the general formula Ia is indicated below.

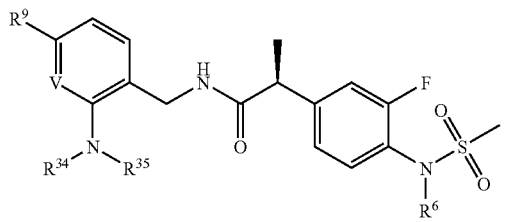

(S)-Ia

The substituted compounds according to the invention of the above-stated general formulae I, Ia, Ib, 1', I'' and I''', hereinafter designated only as compounds of the general formula I, and corresponding stereoisomers may be isolated both in the form of the free bases thereof, the free acids thereof and in the form of corresponding salts, in particular physiologically acceptable salts.

The free bases of the particular substituted compounds according to the invention of the above-stated general formula I and corresponding stereoisomers may, for example, be converted into the corresponding salts, preferably physiologically acceptable salts by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid. The free bases of the respective substituted compounds of the above-stated general formula I and corresponding stereoisomers may likewise be converted into the corresponding physiologically acceptable salts with the free acid or a salt of a sugar substitute, such as for example saccharin, cyclamate or acesulfame.

The free acids of the substituted compounds of the above-stated general formula I and corresponding stereoisomers may correspondingly be converted into the corresponding physiologically acceptable salts by reaction with a suitable base.

Examples which may be mentioned are alkali metal salts, alkaline earth metal salts or ammonium salts $NH_xR_{4-x}]^+$, in which x=0, 1, 2, 3 or 4 and R denotes a linear or branched $C_{1-4}$ alkyl residue.

The substituted compounds according to the invention of the above-stated general formula I and corresponding stereoisomers may optionally, like the corresponding acids, the corresponding bases or salts of these compounds, also be obtained in the form of the solvates thereof, preferably in the form of the hydrates thereof, by conventional methods known to a person skilled in the art.

If the substituted compounds according to the invention of the above-stated general formula I are obtained after the production thereof in the form of a mixture of the stereoisomers thereof, preferably in the form of the racemates thereof or other mixtures of their various enantiomers and/or diastereomers, these may be separated and optionally isolated by conventional methods known to a person skilled in the art. Examples are chromatographic separation methods, in particular liquid chromatography methods at standard pressure or at elevated pressure, preferably MPLC and HPLC methods, and fractional crystallisation methods. Individual enantiomers, for example diastereomeric salts formed by means of HPLC on a chiral stationary phase or by means of crystallisation with chiral acids, such as (+)-tartaric acid, (−)-tartaric acid or (+)-10-camphorsulfonic acid, may here in particular be separated from one another.

The substituted compounds according to the invention of the above-stated general formula I and corresponding stereoisomers as well as in each case the corresponding acids, bases, salts and solvates are toxicologically safe and are therefore suitable as pharmaceutical active ingredients in medicaments.

The present invention accordingly also provides a medicament containing at least one compound according to the invention of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances.

These medicaments according to the invention are suitable in particular for vanilloid receptor 1-(VR1/TRPV1) regulation, preferably for vanilloid receptor 1-(VR1/TRPV1) inhibition and/or for vanilloid receptor 1-(VR1/TRPV1) stimulation.

The medicaments according to the invention are likewise preferably suitable for the prevention and/or treatment of disorders and/or diseases, which are mediated at least in part by vanilloid receptors 1.

The medicament according to the invention is preferably suitable for the treatment and/or prevention of one or more diseases selected from the group consisting of pain selected from the group consisting of acute pain, chronic pain, neuropathic pain and visceral pain; joint pain; hyperalgesia; allodynia; causalgia; migraine; depression; neuropathy; nerve injury; neurodegenerative diseases, preferably selected from the group consisting of multiple sclerosis, Alzheimer's disease, Parkinson's disease and Huntington's chorea; cognitive dysfunction, preferably cognitive deficiency states, particularly preferably memory disorders; epilepsy; airways diseases, preferably selected from the group consisting of asthma, bronchitis and pulmonary inflammation; coughing; urinary incontinence; an overactive bladder (OAB); diseases and/or injuries of the gastrointestinal tract; duodenal ulcers; gastric ulcers; irritable bowel syndrome; strokes; eye irritation; skin irritation; neurotic skin conditions; allergic skin diseases; psoriasis; vitiligo; herpes simplex; inflammation, preferably inflammation of the intestines, the eyes, the bladder, the skin or the nasal mucosa; diarrhoea; pruritus; osteoporosis; arthritis; osteoarthritis; rheumatic diseases; disorders of food intake, preferably selected from the group consisting of bulimia, cachexia, anorexia and obesity; dependency on medicines; abuse of medicines; withdrawal symptoms associated with dependency on medicines; development of tolerance towards medicines, preferably towards natural or synthetic opioids; dependency on drugs; drug abuse; withdrawal symptoms associated with dependency on drugs; dependency on alcohol; alcohol abuse and withdrawal symptoms associated with dependency on alcohol; for diuresis; for antinatriuresis; for influencing the cardiovascular system; for increasing vigilance; for the treatment of wounds and/or burns; for the treatment of severed nerves; for increasing libido; for modulating locomotor activity; for anxiolysis; for local anaesthesia and/or for inhibiting undesired side-effects, preferably selected from the group consisting of hyperthermia, high blood pressure and constriction of bronchial tubes, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

The medicament according to the invention is particularly preferably suitable for the treatment and/or prevention of one or more diseases selected from the group consisting of pain, preferably of pain selected from the group consisting of acute pain, chronic pain, neuropathic pain and visceral pain; joint pain; migraine; depression; neurodegenerative diseases, preferably selected from the group consisting of multiple sclerosis, Alzheimer's disease, Parkinson's disease and Huntington's chorea; cognitive dysfunction, preferably cognitive deficiency states, particularly preferably memory disorders; inflammation, preferably inflammation of the intestines, the eyes, the bladder, the skin or the nasal mucosa; urinary incontinence; an overactive bladder (OAB); dependency on medicines; abuse of medicines; withdrawal symptoms associated with dependency on medicines; development of tolerance towards medicines, preferably development of tolerance towards natural or synthetic opioids; dependency on drugs; drug abuse; withdrawal symptoms associated with dependency on drugs; dependency on alcohol; alcohol abuse and withdrawal symptoms associated with dependency on alcohol.

The medicament according to the invention is very particularly preferably suitable for the treatment and/or prevention of pain, preferably of pain selected from the group consisting of acute pain, chronic pain, neuropathic pain and visceral pain, and/or urinary incontinence.

The present invention also provides the use of at least one compound according to the invention and optionally one or more pharmaceutically acceptable auxiliary substances for the production of a medicament for vanilloid receptor 1-(VR1/TRPV1) regulation, preferably for vanilloid receptor 1-(VR1/TRPV1) inhibition and/or for vanilloid receptor 1-(VR1/TRPV1) stimulation.

It is preferred to use at least one substituted compound according to the invention and optionally one or more pharmaceutically acceptable auxiliary substances for the production of a medicament for the prevention and/or treatment of disorders or diseases which are mediated at least in part by vanilloid receptors 1.

It is particularly preferred to use at least one compound according to the invention and optionally one or more pharmaceutically acceptable auxiliary substances for the production of a medicament for the treatment and/or prevention of one or more diseases selected from the group consisting of pain, preferably of pain selected from the group consisting of acute pain, chronic pain, neuropathic pain and visceral pain and joint pain.

It is particularly preferred to use at least one compound according to the invention and optionally one or more pharmaceutically compatible auxiliary substances for the production of a medicament for the treatment and/or prevention of one or more diseases selected from the group consisting of hyperalgesia; allodynia; causalgia; migraine; depression; neuropathy; nerve injury; neurodegenerative diseases, preferably selected from the group consisting of multiple sclerosis, Alzheimer's disease, Parkinson's disease and Huntington's chorea; cognitive dysfunction, preferably cognitive deficiency states, particularly preferably memory disorders; epilepsy; airways diseases, preferably selected from the group consisting of asthma, bronchitis and pulmonary inflammation; coughing; urinary incontinence; an overactive bladder (OAB); diseases and/or injuries of the gastrointestinal tract; duodenal ulcers; gastric ulcers; irritable bowel syndrome; strokes; eye irritation; skin irritation; neurotic skin conditions; allergic skin diseases; psoriasis; vitiligo; herpes simplex; inflammation, preferably inflammation of the intestines, the eyes, the bladder, the skin or the nasal mucosa; diarrhoea; pruritus; osteoporosis; arthritis; osteoarthritis; rheumatic diseases; disorders of food intake, preferably selected from the group consisting of bulimia, cachexia, anorexia and obesity; dependency on medicines; abuse of medicines; withdrawal symptoms associated with dependency on medicines; development of tolerance towards medicines, preferably towards natural or synthetic opioids; dependency on drugs; drug abuse; withdrawal symptoms associated with dependency on drugs; dependency on alcohol; alcohol abuse and withdrawal symptoms associated with dependency on alcohol; for diuresis; for antinatriuresis; for influencing the cardiovascular system; for increasing vigilance; for the treatment of wounds and/or burns; for the treatment of severed nerves; for increasing libido; for modulating locomotor activity; for anxiolysis; for local anaesthesia and/or for inhibiting undesired side-effects, preferably selected from the group consisting of hyperthermia, high blood pressure and constriction of bronchial tubes, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

It is very particularly preferred to use at least one substituted compound according to the invention and optionally one or more pharmaceutically acceptable auxiliary substances for the production of a medicament for the treatment and/or prevention of one or more diseases selected from the group consisting of pain, preferably of pain selected from the group consisting of acute pain, chronic pain, neuropathic pain and visceral pain; joint pain; migraine; depression; neurodegenerative diseases, preferably selected from the group consisting of multiple sclerosis, Alzheimer's disease, Parkinson's disease and Huntington's chorea; cognitive dysfunction, preferably cognitive deficiency states, particularly preferably memory disorders; inflammation, preferably inflammation of the intestines, the eyes, the bladder, the skin or the nasal mucosa; urinary incontinence; an overactive bladder (OAB); dependency on medicines; abuse of medicines; withdrawal symptoms associated with dependency on medicines; development of tolerance towards medicines, preferably development of tolerance towards natural or synthetic opioids; dependency on drugs; drug abuse; withdrawal symptoms associated with dependency on drugs; dependency on alcohol; alcohol abuse and withdrawal symptoms associated with dependency on alcohol.

It is still further preferred to use at least one substituted compound according to the invention and optionally one or more pharmaceutically acceptable auxiliary substances for the production of a medicament for the treatment and/or prevention of pain, preferably selected from the group consisting of acute pain, chronic pain, neuropathic pain and visceral pain, and/or urinary incontinence.

The medicament according to the invention is suitable for administration to adults and children including small children and babies.

The medicament according to the invention may be formulated as a liquid, semisolid or solid dosage form, for example in the form of solutions for injection, drops, succi, syrups, sprays, suspensions, tablets, patches, capsules, dressings, suppositories, ointments, creams, lotions, gels, emulsions, aerosols or in multiparticulate form, for example in the form of pellets or granules, optionally pressed into tablets, packaged in capsules or suspended in a liquid, and may also be administered as such.

In addition to at least one substituted compound of the above-stated general formula I, optionally in the form of one of the pure stereoisomers thereof, in particular enantiomers or diastereomers, the racemate thereof or in the form of mixtures of the stereoisomers, in particular the enantiomers or diastereomers, in any desired mixing ratio, or optionally in the form of a corresponding salt or in each case in the form of a corresponding solvate, the medicament according to the invention conventionally contains further physiologically acceptable pharmaceutical auxiliary substances, which may for example be selected from the group consisting of matrix materials, fillers, solvents, diluents, surface-active substances, dyes, preservatives, disintegrants, slip agents, lubricants, aromas and binders.

Selection of the physiologically acceptable auxiliary substances and the quantities thereof which are to be used depends upon whether the medicament is to be administered orally, subcutaneously, parenterally, intravenously, intraperitoneally, intradermally, intramuscularly, intranasally, buccally, rectally or topically, for example onto infections of the skin, mucous membranes and eyes. Preparations in the form of tablets, coated tablets, capsules, granules, pellets, drops, succi and syrups are preferred for oral administration, while solutions, suspensions, readily reconstitutible dried preparations and sprays are preferred for parenteral, topical and inhalatory administration. The substituted compounds according to the invention used in the medicament according to the invention in a depot in dissolved form or in a dressing, optionally with the addition of skin penetration promoters, are suitable percutaneous administration preparations. Orally or percutaneously administrable formulations may also release the particular substituted compound according to the invention in delayed manner.

Production of the medicaments according to the invention proceeds with the assistance of conventional means, devices, methods and processes known from the prior art, as are described for example in "Remington's Pharmaceutical Sciences", ed. A. R. Gennaro, 17th ed., Mack Publishing Company, Easton, Pa. (1985), in particular in part 8, chapters 76 to 93. The corresponding description is hereby introduced as a reference and is deemed to be part of the disclosure. The quantity of the particular substituted compounds according to the invention of the above-stated general formula I to be administered to the patient may vary and is for example dependent on the weight or age of the patient and on the mode of administration, the indication and the severity of the complaint. Conventionally, 0.001 to 100 mg/kg, preferably 0.05 to 75 mg/kg, particularly preferably 0.05 to 50 mg/kg of patient body weight of at least one such compound according to the invention are administered.

Pharmacological Methods
I. Functional Investigation on Vanilloid Receptor 1 (VR1/TRPV1 Receptor)

The agonistic or antagonistic action of the substances to be investigated on the vanilloid receptor 1 (VR1/TRPV1) of the rat species may be determined with the following assay. According to this assay, the influx of $Ca^{2+}$ through the receptor channel is quantified with the assistance of a $Ca^{2+}$-sensitive dye (type Fluo-4, Molecular Probes Europe BV, Leiden, Netherlands) in a Fluorescent Imaging Plate Reader (FLIPR, Molecular Devices, Sunnyvale, USA).

Method:
Complete medium: 50 mL HAMS F12 Nutrient Mixture (Gibco Invitrogen GmbH, Karlsruhe, Germany) with 10 vol.

% FCS (foetal calf serum, Gibco Invitrogen GmbH, Karlsruhe, Germany, heat-inactivated);

2 mM L-glutamine (Sigma, Munich, Germany);

1 wt. % AA solution (antibiotic/antimycotic solution, PAA, Pasching, Austria) and 25 ng/mL NGF medium (2.5 S, Gibco Invitrogen GmbH, Karlsruhe, Germany)

Cell culture plate: poly-D-lysine-coated, black 96-hole plates with clear base (96 well black/clear plate, BD Biosciences, Heidelberg, Germany) are additionally coated with laminin (Gibco Invitrogen GmbH, Karlsruhe, Germany), by diluting laminin to a concentration of 100 µg/mL with PBS (Ca—Mg-free PBS, Gibco Invitrogen GmbH, Karlsruhe, Germany). Aliquots with a concentration of 100 µg/mL of laminin are taken and stored at −20° C. The aliquots are diluted with PBS in the ratio of 1:10 to 10 µg/mL of laminin and 50 µL of the solution is pipetted into each well of the cell culture plate. The cell culture plates are incubated for at least two hours at 37° C., the supernatant solution is aspirated and the wells are each washed twice with PBS. The coated cell culture plates are stored with supernatant PBS and this is only removed directly prior to introduction of the cells.

Preparation of the Cells:

The spinal column is removed from decapitated rats and this is placed directly in cold HBSS buffer (Hank's buffered saline solution, Gibco Invitrogen GmbH, Karlsruhe, Germany), i.e. located in an ice bath, combined with 1 vol. % (percent by volume) of an AA solution (antibiotic/antimycotic solution, PAA, Pasching, Austria). The spinal column is severed lengthwise and removed from the spinal canal together with fasciae. The dorsal root ganglia (DRGs) are then removed and in turn stored in cold HBSS buffer combined with 1 vol. % of an AA solution. The DRGs, from which blood residues and spinal nerves have been completely removed, are in each case transferred into 500 µL cold collagenase type 2 (PAA, Pasching, Austria) and incubated for 35 minutes at 37° C. After the addition of 2.5 vol. % trypsin (PAA, Pasching, Austria) incubation at 37° C. is continued for a further 10 minutes. After complete incubation, the enzyme solution is carefully pipetted off and the remaining DRGs are combined in each case with 500 µL of complete medium.

The DRGs are in each case repeatedly suspended, drawn through cannulas no. 1, no. 12 and no. 16 by means of a syringe and transferred into 50 mL Falcon microtubes, these being filled to 15 mL with complete medium. The content of each Falcon microtube is in each case filtered through a 70 µm Falcon filter insert and centrifuged for 10 minutes at 1200 revolutions and room temperature. The resultant pellet is in each case redissolved in 250 µL of complete medium and the cell count is determined.

The number of cells in the suspension is adjusted to $3 \times 10^5$ per mL and a 150 µL portion of this suspension is in each case placed in a well of the cell culture plates which have been coated as described above. The plates are left to stand in the incubator for two to three days at 37° C., 5 vol. % $CO_2$ and 95% relative atmospheric humidity.

The cells are then loaded with 2 µM Fluo-4 and 0.01 vol. % Pluronic F127 (Molecular Probes Europe BV, Leiden, Netherlands) in HBSS buffer (Hank's buffered saline solution, Gibco Invitrogen GmbH, Karlsruhe, Germany) for 30 min at 37° C., washed 3× with HBSS buffer and, after a further 15 minutes' incubation at room temperature, used for $Ca^{2+}$ measurement in the FLIPR assay. $Ca^{2+}$-dependent fluorescence is here measured before and after the addition of substances ($\lambda ex=488$ nm, $\lambda em=540$ nm). Quantification proceeds by measuring the highest fluorescence intensity (FC, fluorescence counts) over time.

FLIPR Assay:

The FLIPR protocol consists of 2 additions of substance. First of all, the compounds to be tested (10 µM) are pipetted onto the cells and $Ca^{2+}$ influx is compared with the control (capsaicin 10 µM). This gives rise to a % activation value relative to the $Ca^{2+}$ signal after addition of 10 µM capsaicin (CP). After 5 minutes' incubation, 100 nM of capsaicin are added and the influx of $Ca^{2+}$ is likewise determined.

Desensitising agonists and antagonists result in suppression of $Ca^{2+}$ influx. The percentage inhibition in comparison with the maximum achievable inhibition with 10 µM capsaicin is calculated.

Three-fold determinations (n=3) are performed and these are repeated in at least 3 independent experiments (N=4).

On the basis of the percentage displacement by different concentrations of the compounds to be tested of the general formula I, $IC_{50}$ inhibition concentrations which bring about 50% displacement of capsaicin were calculated. $K_i$ values for the test substances were obtained by conversion using the Cheng-Prusoff equation (Cheng, Prusoff; Biochem. Pharmacol. 22, 3099-3108, 1973).

II. Functional Investigations on Vanilloid Receptor (VR1)

The agonistic or antagonistic action of the substances to be investigated on the vanilloid receptor (VR1) may also be determined with the following assay. According to this assay, the influx of $Ca^{2+}$ through the channel is quantified with the assistance of a $Ca^{2+}$-sensitive dye (type Fluo-4, Molecular Probes Europe BV, Leiden, Netherlands) in a Fluorescent Imaging Plate Reader (FLIPR, Molecular Devices, Sunnyvale, USA).

Method:

Chinese hamster ovary cells (CHO K1 cells, European Collection of Cell Cultures (ECACC), Great Britain) are stably transfected with the VR1 gene. For functional investigations, these cells are plated out onto poly-D-lysine-coated, black 96-hole plates with a clear base (BD Biosciences, Heidelberg, Germany) at a density of 25,000 cells/hole. The cells are incubated overnight at 37° C. and 5% $CO_2$ in a culture medium (Ham's Nutrient Mixture F12, 10 vol. % FCS (foetal calf serum), 18 µg/mL L-proline). On the following day, the cells are incubated with Fluo-4 (Fluo-4 2 µM, Pluronic F127 0.01 vol. %, Molecular Probes in HBSS (Hank's buffered saline solution), Gibco Invitrogen GmbH, Karlsruhe, Germany) for 30 minutes at 37° C. The plates are then washed 3 times with HBSS buffer and, after a further 15 minutes' incubation at room temperature, used for $Ca^{2+}$ measurement in the FLIPR. $Ca^{2+}$-dependent fluorescence is here measured before and after the addition of the substances to be investigated (wavelength $\lambda_{ex}=488$ nm, $\lambda_{em}=540$ nm). Quantification proceeds by measuring the highest fluorescence intensity (FC, fluorescence counts) over time.

FLIPR Assay:

The FLIPR protocol consists of 2 additions of substance. The substances to be tested (10 µM) are firstly pipetted onto the cells and $Ca^{2+}$ influx is compared with the control (capsaicin 10 µM) (% activation relative to the $Ca^{2+}$ signal after addition of 10 µM of capsaicin). After 5 minutes' incubation, 100 nM of capsaicin are added and the influx of $Ca^{2+}$ is likewise determined.

Desensitising agonists and antagonists resulted in suppression of $Ca^{2+}$ influx. The percentage inhibition in comparison with the maximum achievable inhibition with 10 µM capsaicin is calculated.

On the basis of the percentage displacement by different concentrations of the compounds to be tested of the general formula I, $IC_{50}$ inhibition concentrations which bring about 50% displacement of capsaicin were calculated. $K_i$ values for the test substances were obtained by conversion using the Cheng-Prusoff equation (Cheng, Prusoff; Biochem. Pharmacol. 22, 3099-3108, 1973).

III. b. Formaldehyde Test in Mice

The investigation for determining the antinociceptive action of the compounds according to the invention is performed using the formaldehyde test on male mice (NMRI, 20 to 30 g body weight, Iffa, Credo, Belgium).

In the formaldehyde test, according to D. Dubuisson et al., Pain 1977, 4, 161-174 a distinction is drawn between the first (early) phase (0 to 15 minutes after the formaldehyde injection) and the second (late) phase (15 to 60 minutes after the formaldehyde injection). The early phase, being a direct response to the formaldehyde injection, is considered to be a model for acute pain, while the late phase is considered to be a model for persistent (chronic) pain (T. J. Coderre, et al., Pain 1993, 52, 259-285). The corresponding literature descriptions are hereby introduced as a reference and are deemed to be part of the disclosure.

The compounds according to the invention are investigated in the second phase of the formaldehyde test in order to obtain information concerning the effects of the substances on chronic/inflammatory pain.

The administration time of the compounds according to the invention prior to the formaldehyde injection is selected as a function of the mode of administration of the compounds according to the invention. Intravenous administration of 10 mg/kg body weight of the test substances proceeds 5 minutes prior to the formaldehyde injection. This is effected by a one-off subcutaneous formaldehyde injection (20 µL, 1% aqueous solution) into the dorsal side the right hand hind paw, such that, in the case of freely mobile test animals, a nociceptive reaction is induced, which manifests itself in marked licking and biting of the relevant paw.

Then, the nociceptive behaviour of the animals is observed and recorded continuously for an investigation period of three minutes in the second (late) phase of the formaldehyde test (21 to 24 minutes after the formaldehyde injection).

Quantification of the pain behaviour proceeds by summation of the seconds in which the animals licked and bit the relevant paw during the investigation period.

The comparison is made in each case with control animals, which, instead of compounds according to the invention, received vehicle (0.9% aqueous sodium chloride soln.) before administration of the formaldehyde. On the basis of the quantification of the pain behaviour, the substance effect in the formaldehyde test is determined in percent as a change compared with the corresponding control.

After the injection of substances which have an antinociceptive action in the formaldehyde test, the described behaviours of the animals, i.e. licking and biting, are reduced or eliminated.

IV. c) Investigation of Analgesic Efficacy by the Writhing Test

Investigation of the compounds according to the invention of the general formula I for analgesic efficacy was performed by phenylquinone-induced writhing in the mouse, modified after I. C. Hendershot and J. Forsaith (1959) J. Pharmacol. Exp. There. 125, 237-240. The corresponding literature description is hereby introduced as a reference and is deemed to be part of the disclosure.

Male NMRI mice weighing from 25 to 30 g were used for this purpose. Groups of 10 animals per compound dose received, 10 minutes after intravenous administration of the compounds to be tested, 0.3 mL/mouse of a 0.02% aqueous solution of phenylquinone (phenylbenzoquinone, Sigma, Deisenhofen, Germany; solution prepared with addition of 5% of ethanol and stored in a water bath at 45° C.) administered intraperitoneally. The animals were placed individually in observation cages. A push button counter was used to record the number of pain-induced stretching movements (writhing reactions=straightening of the torso with stretching of the rear extremities) for 5-20 minutes after phenylquinone administration. The control was provided by animals which had received only physiological saline. All the compounds were tested at the standard dosage of 10 mg/kg.

V. Hypothermia Assay in Mice

Description of Method:

The hypothermia assay is carried out on male NMRI mice (weight 25-35 grams, breeder IFFA CREDO, Brussels, Belgium). The animals were kept under standardised conditions: light/dark cycle (06:00 to 18:00 light phase; 18:00 to 06:00 dark phase), room temperature 19-22° C., relative humidity 35-70%, 15 air exchanges per hour, air movement <0.2 m/sec. The animals received standard feed (ssniff R/M maintenance, ssniff Spezialdiätten GmbH, Soest, Germany) and tap water. Water and feed were withdrawn during the test. All the animals were used only once in the test. The animals had a habituation phase of at least 5 days.

Acute administration of capsaicin (VR-1 agonist) leads to a drop in core body temperature in rats and mice by stimulation of heat sensors. Only specifically acting VR-1-receptor antagonists are capable of antagonising capsaicin-induced hypothermia. Morphine-induced hypothermia, in contrast, is not antagonised by VR-1 antagonists. This model is therefore suitable for identifying substances with VR-1 antagonistic properties from their action on the body temperature.

Core body temperature was measured using a digital thermometer (Thermalert TH-5, physitemp, Clifton N.J., USA). The sensor is here inserted into the animal's rectum.

Body temperature is measured twice for each animal at an interval of approx. half an hour as an individual baseline value. One group of animals (n=6 to 10) then receives intraperitoneal (i.p.) administration of capsaicin 3 mg/kg and vehicle (control group). Another group of animals receives the substance to be tested (i.v. or per os) and additionally capsaicin (3 mg/kg) i.p. The test substance is administered i.v. 10 minutes or per os 15 minutes before the capsaicin. Body temperature is then measured 7.5/15 and 30 min after capsaicin (i.v.+i.p.) or 15/30/60/90/120 min (per os+i.p.) after capsaicin. In addition, one group of animals is treated only with the test substance and one group only with vehicle.

The measured values are evaluated and presented as a mean+/−SEM of the absolute values on a graph. The antagonistic action is calculated as a percentage reduction in capsaicin-induced hypothermia.

VI. Neuropathic Pain in Mice

Efficacy against neuropathic pain was investigated in the Bennett model (chronic constriction injury; Bennett and Xie, 1988, Pain 33: 87-107).

NMRI mice weighing 16-18 g are provided under Ketavet-Rompun anaesthesia with three loose ligatures of the right ischial nerve. On the paw innervated by the damaged nerve, the animals develop hypersensitivity which, after one week's convalescence, is quantified over a period of approx. three weeks by means of a cold metal plate at 4° C. (cold allodynia). The animals are observed on this plate for a period of 2 min. and the number of withdrawal responses by the damaged paw is measured. Relative to the preliminary value prior to administration of the substance, the action of the substance is determined at different occasions over a given period (for example 15, 30, 45, 60 min. after administration) and the resultant area under the curve (AUC) and/or the inhibition of cold allodynia at the individual measuring points is stated as a percentage action relative to the vehicle control (AUC) or to the initial value (individual measurement points). The size of the group is n=10, the significance of an antiallodynic action (*=p<0.05) is determined with reference to an analysis of variance with repeated measurement and post hoc Bonferroni analysis.

The invention will be explained below with reference to a number of examples. These explanations are given merely by way of example and do not restrict the general concept of the invention.

EXAMPLES

The yields of the compounds produced have not been optimised.

All temperatures are uncorrected.

The term "equivalents" means molar equivalents, "RT" means room temperature, "M" and "N" are concentrations stated in mol/l, "aq." means aqueous, "sat." means saturated, "soln." means solution, Other Abbreviations

| | |
|---|---|
| DMF | N,N-dimethylformamide |
| EDCI | N-ethyl-N'-(3-dimethylaminopropyl)-carbodiimide hydrochloride |
| EA | ethyl acetate |
| H$_2$O | water |
| MeOH | methanol |

The chemicals and solvents used were purchased from conventional suppliers (Acros, Avocado, Aldrich, Bachem, Fluka, Lancaster, Maybridge, Merck, Sigma, TCI, Oakwood etc.) or synthesised by conventional methods known to a person skilled in the art.

Silica gel 60 (0.0-0-0.063 mm) from E. Merck, Darmstadt, was used as the stationary phase for the column chromatography.

Thin-layer chromatography was performed with pre-coated silica gel 60 F 254 HPTLC plates from E. Merck, Darmstadt.

The mixture ratios for solvents, mobile solvents or for chromatographic investigations are always stated in volume/volume.

Analysis was performed by mass spectroscopy and NMR.

1. General Method of Preparing Amines of the General Formula V-A

Amines of the general formula V-A are prepared as illustrated in the following Scheme 1.

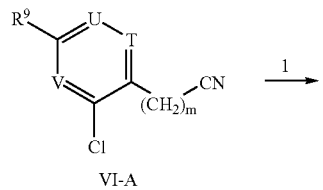

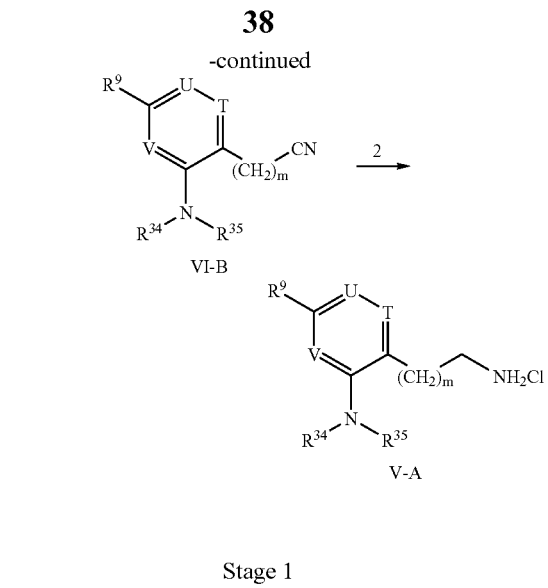

Stage 1

Preparation of Nitrites of the General Formula VI-B

Method A:

Compounds of the general formula VI-A (1 equivalent), in which R$^9$, U, T and V have the above-stated meanings and m denotes 0, 1, 2 or 3, are stirred with an amine of the general formula HNR$^{34}$R$^{35}$ (6 equivalents) for 48 hours at RT. The reaction mixture is combined with 1 N hydrochloric acid and extracted repeatedly with EA. The aqueous phase is saturated with NaCl and then extracted again with EA. The combined organic phases are washed with 1 N hydrochloric acid and with a sat. aq. NaCl soln., dried over MgSO$_4$ and the solvent was removed under a vacuum.

Method B:

Compounds of the general formula VI-A (1 equivalent), in which R$^9$, U, T and V have the above-stated meanings and m denotes 0, 1, 2 or 3, are stirred with an amine of the general formula HNR$^{34}$R$^{35}$ (2 equivalents) and DBU [1,8-diaza-bicyclo[5.4.0]undec-7-ene] (2 equivalents) in acetonitrile (7 mL per mmol of the compound of formula VI-A) for 12 hours at RT. The reaction mixture is extracted repeatedly with EA. The combined organic phases are washed with sat. aq. NaCl solution, dried over MgSO$_4$ and the solvent was removed under a vacuum. The residue is purified in each case by column chromatography (SiO$_2$, different mixtures of hexane/EA).

The following compounds were produced using Method B.

6-(trifluoromethyl)-2-(4-methylpiperidin-1-yl)pyridine-3-carbonitrile

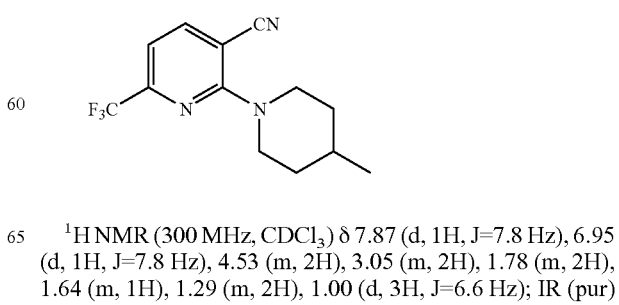

$^1$H NMR (300 MHz, CDCl$_3$) δ 7.87 (d, 1H, J=7.8 Hz), 6.95 (d, 1H, J=7.8 Hz), 4.53 (m, 2H), 3.05 (m, 2H), 1.78 (m, 2H), 1.64 (m, 1H), 1.29 (m, 2H), 1.00 (d, 3H, J=6.6 Hz); IR (pur)

2926, 2852, 2218, 1590, 1497, 1456, 1324, 1237, 1186, 1147, 1082, 963 cm$^{-1}$; MS (FAB) m/z 270 (M+H)

N-(3'-cyano-6'-trifluoromethyl-3,4,5,6-tetrahydro-2H-[1,2']bipyridinyl-4-yl)-N-phenyl-propionamide

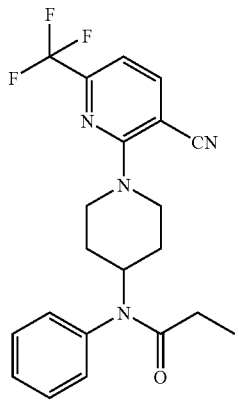

$^1$H NMR (300 MHz, CDCl$_3$) δ 7.85 (d, 1H, J=7.8 Hz), 7.41 (m, 3H), 7.11 (m, 2H), 6.95 (d, 2H, J=7.8 Hz), 4.96 (m, 1H), 4.61 (m, 2H), 3.14 (m, 2H), 1.96 (m, 4H), 1.46 (m, 2H), 1.03 (t, 3H, J=7.5 Hz); MS (FAB) m/z 403 (M+H)

Stage 2

Method 1

Compounds of the general formula VI-B (5 mmol), in which R$^9$, R$^{34}$, R$^{35}$, U, T and V have the above-stated meanings and m denotes 0, 1, 2 or 3, palladium on carbon (10%, 500 mg) and concentrated hydrochloric acid (3 mL) are dissolved in MeOH (30 mL) and exposed to a hydrogen atmosphere for 6 hours at RT. The reaction mixture is filtered through Celite and the filtrate is evaporated under a vacuum. The residue is purified by means of flash chromatography (SiO$_2$, EA).

Method 2:

Compounds of the general formula VI-B (2 mmol), in which R$^9$, R$^{34}$, R$^{35}$, U, T and V have the above-stated meanings and m denotes 0, 1, 2 or 3, are dissolved in THF (10 mL, 10 mL) and BH$_3$.S(CH$_3$)$_2$ [2.0 M in THF, 3 mL, 3 equivalents] is added thereto. The reaction mixture is heated to reflux for 8 hours, aq. HCl (2 N) is added thereto and the reaction mixture is again heated to reflux for 30 minutes. The reaction mixture is combined with aq. sodium hydroxide solution (2 N) and washed with EA. The combined organic phases are washed with a sat. aq. NaCl solution and dried over magnesium sulfate. The solvent is removed under a vacuum and the residue is purified by column chromatography (SiO$_2$, different mixture of dichloromethane and methanol as mobile solvent).

The following compounds were obtained using Method 2.

(6-(trifluoromethyl)-2-(4-methylpiperidin-1-yl)pyridin-3-yl)methanamine

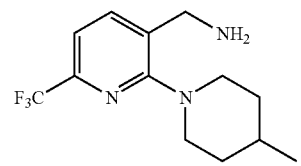

$^1$H NMR (300 MHz, CDCl$_3$) δ 7.89 (d, 1H, J=7.8 Hz), 7.33 (d, 1H, J=7.8 Hz), 3.88 (s, 2H), 3.39 (m, 2H), 2.83 (m, 2H), 1.75 (m, 2H), 1.55 (m, 1H), 1.38 (m, 2H), 1.00 (d, 3H, J=6.6 Hz); MS (FAB) m/z 274 (M+H)

3'-aminomethyl-4-phenyl-6'-trifluoromethyl-3,4,5,6-tetrahydro-2H-[1,2']bipyridinyl-4-carboxylic acid ethyl ester

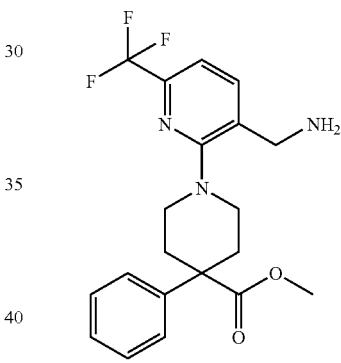

$^1$H NMR (300 MHz, CDCl$_3$) δ 7.83 (d, 1H, J=7.5 Hz), 7.45 (m, 2H), 7.35 (m, 3H), 7.26 (d, 1H, J=8.1 Hz), 4.15 (q, 2H, J=7.2 Hz), 4.03 (s, 2H), 3.47 (m, 2H), 3.08 (m, 2H), 2.69 (m, 2H), 2.10 (m, 2H), 1.21 (t, 3H, J=7.2 Hz); MS (FAB) m/z 408 (M+H)

2. General Method of Preparing Amines of the General Formula V-E

Amines of the general formula V-E are prepared as illustrated in the following Scheme 2.

Scheme 2.

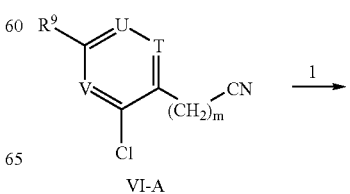

VI-A

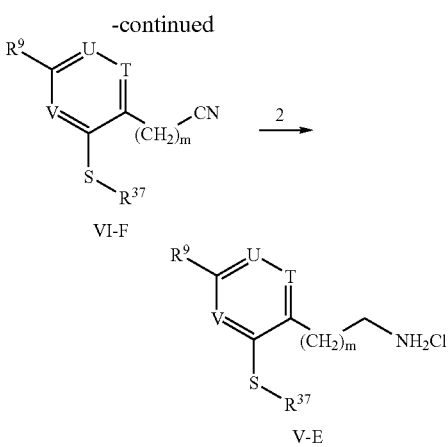

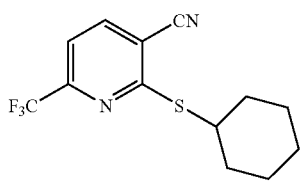

Stage 1

Synthesis of 2-(cyclohexylthio)-6-(trifluoromethyl) nicotinonitrile 1.3 equivalents of NaH (4.9 g, 0.124 mol) were dissolved in 50 mL DMF under a nitrogen atmosphere. After the addition of 1.2 equivalents of cyclohexanethiol (14.2 mL, 0.116 mol), stirring was performed at room temperature for 1.5 h. The resultant suspension was cooled to 10° C. and 1 equivalent of 2-chloro-6-(trifluoromethyl)nicotinonitrile (20 g, 0.096 mol) in 50 mL DMF was added dropwise and stirred for 2 h at room temperature. The reaction mixture was quenched with sat. aq. $NH_4Cl$ soln., diluted with 1 l of water and extracted repeatedly with EA (3×200 mL). The combined organic phases were washed with a sat. aq. NaCl soln., dried over $MgSO_4$ and evaporated under a vacuum. Purification performed by column chromatography (silica gel, 100-200 mesh, eluent: 2% EA in hexane) resulted in 26 g (93.8%) of product.

$^1$H NMR (300 MHz, $CDCl_3$) δ 7.94 (d, 1H, J=7.9 Hz), 7.34 (d, 1H, J=7.9 Hz), 4.00 (m, 1H), 1.90-2.14 (m, 2H), 1.42-1.88 (m, 8H)

IR (neat) 2930, 2854, 2232, 1643, 1573, 1447, 1334, 1245, 1186, 1149, 1107, 851 $cm^{-1}$ MS (FAB) m/z 287 (M+H)

Stage 2

Synthesis of (2-(cyclohexylthio)-6-(trifluoromethyl) pyridin-3-yl)methanamine dihydrochloride The nitrile (26 g, 0.091 mol) was dissolved under a nitrogen atmosphere in 600 mL of THF and cooled to 5° C. $BH_3$-DMS (13.78 g, 0.182 mol) was added dropwise and refluxed for 20 h. After cooling to 5° C., the reaction batch was quenched with 100 mL of MeOH and stirred for 15 minutes at room temperature. Then di-tert.-butyl dicarbonate (29.7 g, 0.136 mol) was added and stirring was performed for 30 min at room temperature. After removal of the solvent under a vacuum, the crude product was purified by column chromatography (silica gel, 100-200, mesh, eluent: 10% EA in hexane) and 23.4 g (66%) of product was obtained.

The crude product was dissolved in 120 mL sat. HCl-dioxane soln. and stirred for 6 h at room temperature. After removal of the solvent under a vacuum, the solid was washed with 10% EA in hexane (2×100 mL) and filtered out.

Yield: 17 g (88.8%)

$^1$H NMR (DMSO-$d_6$, 400 MHz): δ 8.8 (s, 2H), 8.05 (d, 1H), 7.76 (d, 1H), 4.01 (s, 1H), 3.86-3.93 (m, 1H), 2.02-2.08 (m, 2H), 1.71-1.74 (m, 2H), 1.40-1.60 (m, 6H).

3. General Method of Preparing Amines of the General Formula V-B

Amines of the general formula V-B are prepared as illustrated in the following Scheme 3.

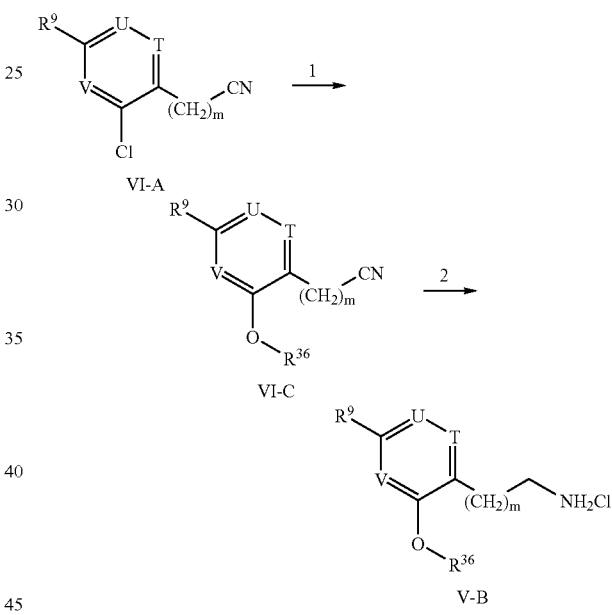

Stage 1

Preparation of Nitriles of the General Formula VI-C

Compounds of the general formula VI-A (1 equivalent), in which $R^9$, U, T and V have the above-stated meanings and m denotes 0, 1, 2 or 3, are stirred with an alcohol of the general formula HO—$R^{36}$ (3.5 equivalents) and DBU [1,8-diaza-bicyclo[5.4.0]undec-7-ene] (3.5 equivalents) in acetonitrile (7 mL per mmol of the compound of formula VI-A) for 12 hours at RT. The reaction mixture is extracted repeatedly with EA. The combined organic phases are washed with sat. aq. NaCl solution, dried over $MgSO_4$ and the solvent was removed under a vacuum. The residue is purified in each case by column chromatography ($SiO_2$, different mixtures of hexane/ EA).

Method 2:

Compounds of the general formula VI-C (2 mmol), in which $R^9$, $R^{36}$, U, T and V have the above-stated meanings and m denotes 0, 1, 2 or 3, are dissolved in THF (10 mL, 10 mL) and $BH_3 \cdot S(CH_3)_2$ [2.0 M in THF, 3 mL, 3 equivalents] is added thereto. The reaction mixture is heated to reflux for 8 hours, aq. HCl (2 N) is added thereto and the reaction mixture is again heated to reflux for 30 minutes. The reaction mixture is combined with aq. sodium hydroxide solution (2 N) and washed with EA. The combined organic phases are washed with a sat. aq. NaCl solution and dried over magnesium sulfate. The solvent is removed under a vacuum and the residue is purified by column chromatography ($SiO_2$, different mixture of dichloromethane and methanol as mobile solvent).

Method 3:

Compounds of the general formula VI-C (1.5 mmol), in which $R^9$, $R^{36}$, U, T and V have the above-stated meanings and m denotes 0, 1, 2 or 3, are dissolved in diethyl ether (3 mL) and a suspension of lithium aluminium hydride (3 mmol) in ether (5 mL) is added slowly dropwise at 0° C. The reaction mixture is heated to reflux for 4 hours and methanol and then 1 N aq. NaOH solution are added slowly dropwise at 0° C. The reaction mixture is diluted with methanol and filtered through Celite. The solvent is removed under a vacuum and the residue is purified by column chromatography ($SiO_2$, different mixture of dichloromethane and methanol as mobile solvent).

4. General Method of Preparing Amines of the General Formula V-C

Amines of the general formula V-C are prepared as illustrated in the following Scheme 4.

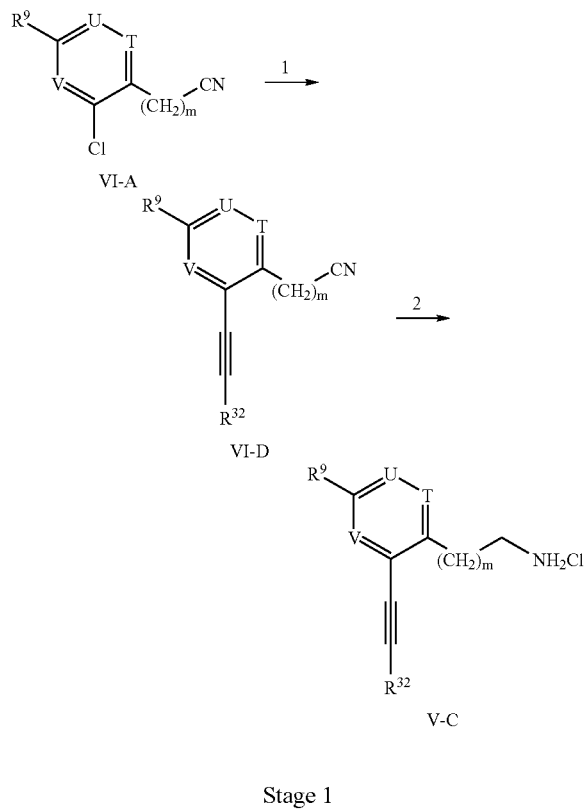

Stage 1

Preparation of Nitrites of the General Formula VI-D

Compounds of the general formula VI-A (1 equivalent), in which $R^9$, U, T and V have the above-stated meanings and m denotes 0, 1, 2 or 3, are dissolved with bis(triphenylphosphine)palladium dichloride (7 mol %) and copper(I) iodide (14 mol %) in 1-methyl-2-pyrrolidinone (7 mL per mmol of compound of the general formula VI-A). After 10 minutes the alkyne of the general formula $HC\equiv C-R^{32}$ (3.5 equivalents) and N,N-diisopropylethylamine (2 equivalents) are added and the reaction mixture is stirred for 12 h at a temperature of between 90 and 110° C. The reaction mixture is filtered through Celite and extracted repeatedly with EA. The combined organic phases are washed with sat. aq. NaCl solution, dried over $MgSO_4$ and the solvent was removed under a vacuum. The residue is purified in each case by column chromatography ($SiO_2$, different mixtures of hexane/EA).

5. General Method of Preparing Amines of the General Formula V-D

Amines of the general formula V-D are prepared as illustrated in the following Scheme 5.

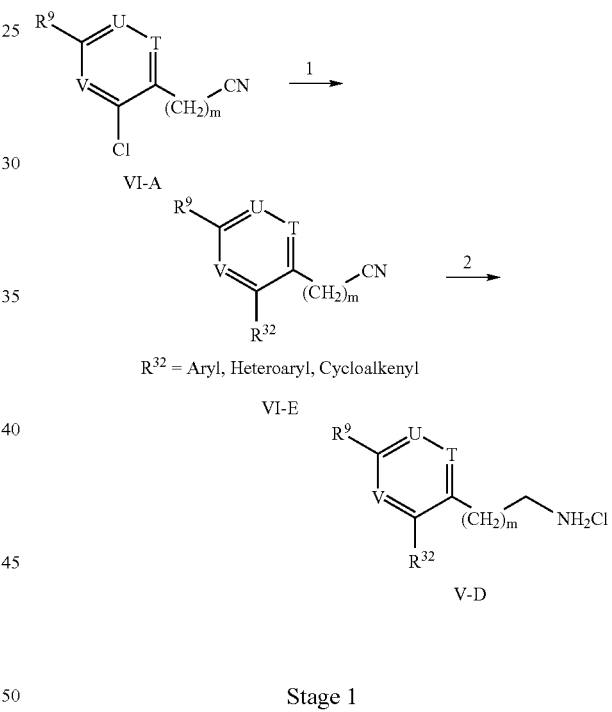

Stage 1

Preparation of Nitrites of the General Formula VI-E

Compounds of the general formula VI-A (1 equivalent), in which $R^9$, U, T and V have the above-stated meanings and m denotes 0, 1, 2 or 3, are stirred with palladium dichloride (5 mol %) and a compound of the general formula $R^{32}-B(OH)_2$ (2 equivalents), in which $R^{32}$ denotes aryl, heteroaryl or cycloalkenyl, in a solvent mixture of toluene/dioxane/2 N aq. sodium carbonate solution (20 mL per 1 mmol compounds of the general formula VI-A). The reaction mixture is heated to reflux for 12 h and filtered through Celite. The combined organic phases are dried over magnesium sulfate and the solvent is removed under a vacuum. The residue is purified by column chromatography ($SiO_2$, different solvent mixtures of hexane and EA).

Stage 2

Method 1

Compounds of the general formula VI-E (5 mmol), in which $R^9$, $R^{32}$, U, T and V have the above-stated meanings and m denotes 0, 1, 2 or 3, palladium on carbon (10%, 500 mg) and concentrated hydrochloric acid (3 mL) are dissolved in MeOH (30 mL) and exposed to a hydrogen atmosphere for 6 hours at RT. The reaction mixture is filtered through Celite and the filtrate is evaporated under a vacuum. The residue is purified by means of flash chromatography ($SiO_2$, EA).

Method 2:

Compounds of the general formula VI-E (2 mmol), in which $R^9$, $R^{32}$, U, T and V have the above-stated meanings and m denotes 0, 1, 2 or 3, are dissolved in THF (10 mL, 10 mL) and $BH_3 \cdot S(CH_3)_2$ [2.0 M in THF, 3 mL, 3 equivalents] is added. The reaction mixture is heated to reflux for 8 hours, aq. HCl (2 N) is added thereto and the reaction mixture is again heated to reflux for 30 minutes. The reaction mixture is combined with aq. sodium hydroxide solution (2 N) and washed with EA. The combined organic phases are washed with a sat. aq. NaCl solution and dried over magnesium sulfate. The solvent is removed under a vacuum and the residue is purified by column chromatography ($SiO_2$, different mixture of dichloromethane and methanol as mobile solvent).

6. General Method of Preparing Carboxylic Acids of the General Formula VIIa

Carboxylic acids of the general formula VIIIa are prepared as illustrated in the following Scheme 6.

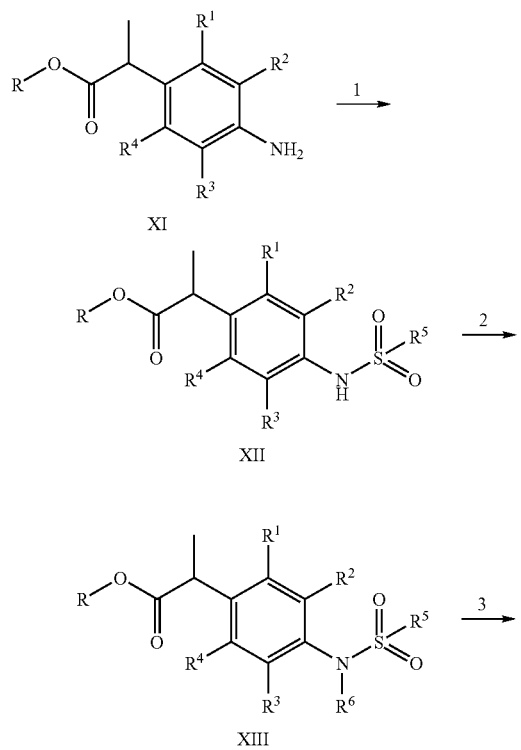

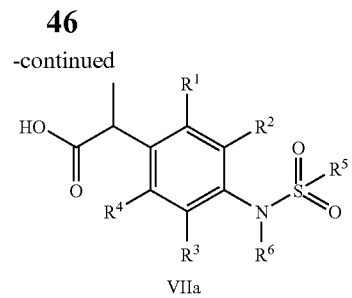

Stage 1

Compounds of the general formula XI (7 mmol), in which $R^1$, $R^2$, $R^3$ and $R^4$ have the above-stated meanings and R denotes a linear or branched $C_{1-6}$ alkyl residue, are stirred with compounds of the general formula Cl—S(=O)$_2$—$R^5$ (8 mmol), in which $R^5$ has the above-stated meaning, for 10 minutes at 0° C. and then 3 hours at room temperature in pyridine (10 mL). The reaction mixture is redissolved in dichloromethane and aq. HCl (1 N), the organic phase is separated and the solvent removed under a vacuum. The residue is in each case crystallised from dichloromethane/hexane mixtures.

Stage 2

1 equivalent of the compounds of the general formula XII, in which $R^1$, $R^2$, $R^3$, $R^4$ and $R^5$ have the above-stated meanings and R denotes a linear or branched $C_{1-6}$ alkyl residue, was added to a suspension of 1.25 equivalents NaH (60%) in DMF and the suspension was stirred for 30 minutes at room temperature. 3.5 equivalents of a compound of the general formula $R^6$—I, in which $R^6$ denotes a linear or branched $C_{1-6}$ alkyl residue, were added to this reaction mixture in portions and the suspension was stirred for 1.5 h at 100° C. and slowly cooled to room temperature. After the addition of water, the reaction mixture was extracted twice with EA, the combined organic phases washed repeatedly with sat. aq. NaCl-soln., dried over $MgSO_4$ and evaporated. The crude product was further processed directly in the next step.

Stage 3

Compounds of the general formula XIII (5 mmol), in which $R^1$, $R^2$, $R^3$, $R^4$, $R^5$ and $R^6$ have the above-stated meanings and R denotes a linear or branched $C_{1-6}$ alkyl residue, are stirred with lithium hydroxide monohydrate (15 mmol) in a solvent mixture of water and tetrahydrofuran (1:2, 24 mL) for 4 hours at 40° C. The reaction mixture is redissolved in dichloromethane and water, combined with aq. hydrochloric acid (1 N) and extracted repeatedly with dichloromethane. The combined organic phases are washed with a sat. aq. NaCl solution and dried over sodium sulfate. The solvent is removed under a vacuum and the residue is crystallised from ethyl acetate/hexane mixtures.

7. General Method of Reacting Amines of the General Formulae V or X with Carboxylic Acids of the General Formula VII The acid of the general formula VII (1 equivalent), the amine of the general formulae V or X (1.2 equivalents) and EDCI (1.2 equivalents) are stirred in DMF (10 mmol acid in 20 mL) for 12 hours at RT and then water is added thereto. The reaction mixture is extracted repeatedly with EA, the aqueous phase is saturated with NaCl and then re-extracted with EA. The combined organic phases are washed with 1 N hydrochloric acid and a sat. aq. NaCl soln., dried over MgSO$_4$ and the solvent is removed under a vacuum. The residue is purified by means of flash chromatography (SiO$_2$, EA/hexane 1:2).

The following exemplary compounds were obtained according to the above-stated general method.

Exemplary Compound 3

2-(3-fluoro-4-(N-methylmethylsulfonamido)phenyl)-N-((2-(4-methylpiperidin-1-yl)-6-(trifluoromethyl)pyridin-3-yl)methyl)propanamide

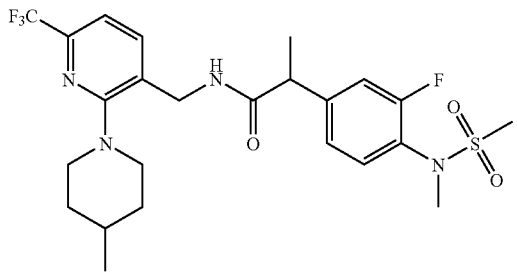

$^1$H NMR (300 MHz, CDCl$_3$) δ 7.47 (d, 1H, J=7.8 Hz), 7.38 (dd, 1H, J=8.1, 8.1 Hz), 7.21 (d, 1H, J=7.8 Hz), 7.07-7.14 (m, 2H), 6.31 (bt, 1H), 4.47 (d, 2H, J=5.7 Hz), 3.57 (q, 1H, J=6.9 Hz), 3.23-3.55 (m, 5H), 3.95 (s, 3H), 2.81 (m, 2H), 1.73 (m, 2H) 1.52 (d, 3H, J=6.9 Hz), 1.17-1.34 (m, 3H), 0.98 (d, 3H, J=6.3 Hz)

IR (KBr) 3245, 2923, 1651, 1508, 1443, 1330, 1222, 1159, 1111 cm$^{-1}$

MS (FAB) m/z 531 (M+H)

8. General Method of Preparing Compounds of the General Formula I, in which R$^6$ Denotes —C(=O)—R$^{28}$ 1 equivalent of a compound of the general formula I, in which R$^6$ denotes hydrogen, and 1 equivalent of the corresponding freshly distilled carboxylic anhydride of the general formula R$^{28}$—C(=O)—O—C(=O)—R$^{28}$ were dissolved in a small amount of dichloromethane and combined with a few drops of H$_2$SO$_4$ and stirred for 2 h at 100° C. After cooling to room temperature, the reaction mixture was poured onto ice water and the aqueous phase was extracted twice with dichloromethane. The combined organic phases were deacidified with soda solution, washed with water and dried over MgSO$_4$. After removal of the solvent under a vacuum, the crude product was purified by column chromatography (silica gel: mesh 100-200, eluent: 15% EA in hexane).

Exemplary Compound 1

N-(2-fluoro-4-(1-oxo-1-((2-(4-(N-phenylpropionamido)piperidin-1-yl)-6-(trifluoromethyl)pyridin-3-yl)methylamino)propan-2-yl)phenyl)-N-(methylsulfonyl)propionamide

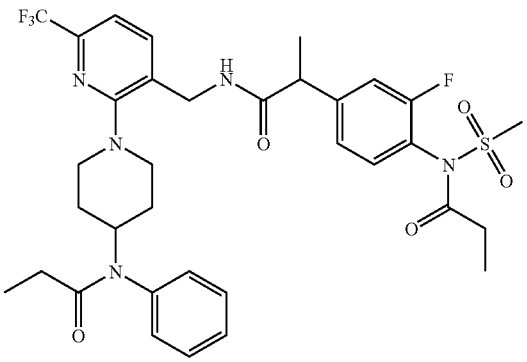

$^1$H NMR (300 MHz, CDCl$_3$) δ 7.29-7.44 (m, 5H), 7.10-7.19 (m, 5H), 6.24 (bt, 1H), 4.78 (m, 1H), 4.38 (d, 2H, J=5.1 Hz), 3.50 (q, 1H, J=6.9 Hz), 3.46 (s, 3H), 3.35-3.39 (m, 2H), 2.97-3.04 (m, 2H), 1.89-1.96 (m, 4H) 1.45-1.65 (m, 9H), 0.99-1.10 (m, 6H)

IR (KBr) 2934, 1716, 1644, 1592, 1504, 1415, 1361, 1277, 1160, 963, 915, 732 cm$^{-1}$

MS (FAB) m/z 706 (M+H)

Exemplary Compound 2

2-(3-fluoro-4-(N-(methylsulfonyl)acetamido)phenyl)-N-((2-(4-methylpiperidin-1-yl)-6-(trifluoromethyl)pyridin-3-yl)methyl)propanamide

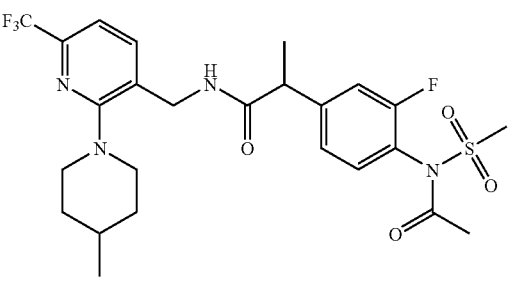

$^1$H NMR (300 MHz, CDCl$_3$) δ7.42 (d, 1H, J=7.8 Hz), 7.31 (dd, 1H, J=8.1, 8.1 Hz), 7.17-7.25 (m, 3H), 6.37 (bt, 1H), 4.46 (m, 2H), 3.57 (q, 1H, J=6.9 Hz), 3.43 (s, 3H), 3.31 (m, 2H), 2.82 (m, 2H), 1.98 (s, 3H), 1.72 (m, 2H) 1.54 (d, 3H, J=7.2 Hz), 1.21-1.29 (m, 3H), 0.96 (d, 3H, J=6.6 Hz)

IR (KBr) 3265, 2933, 1652, 1519, 1433, 1327, 1223, 1161, 1105 cm$^{-1}$

MS (FAB) m/z 559 (M+H)

The following additional illustrative example compounds were obtained using the above-described methods.

[4] N-(4-tert.-butylbenzyl)-2-(3-fluoro-4-(N-methylmethylsulfonamido)phenyl)propanamide,
[5] (S)-N-(4-tert.-butylbenzyl)-2-(3-fluoro-4-(N-methylmethylsulfonamido)phenyl)propanamide,
[6] (S)-N-(4-tert.-butylbenzyl)-2-(4-(N-ethylmethylsulfonamido)-3-fluorophenyl)propanamide,
[7] N-((2-(cyclohexylthio)-6-(trifluoromethyl)pyridin-3-yl)methyl)-2-(3-fluoro-4-(N-methylmethylsulfonamido)phenyl)propanamide,
[8] N-((2-(cyclohexylthio)-6-(trifluoromethyl)pyridin-3-yl)methyl)-2-(4-(N-ethylmethylsulfonamido)-3-fluorophenyl)propanamide,
[9] 2-(4-(N-ethylmethylsulfonamido)-3-fluorophenyl)-N-((2-(4-methylpiperidin-1-yl)-6-(trifluoromethyl)pyridin-3-yl)methyl)propanamide,
[10] N-((6-tert.-butyl-2-(4-methylpiperidin-1-yl)pyridin-3-yl)methyl)-2-(3-fluoro-4-(N-methylmethylsulfonamido)phenyl)propanamide,
[11] N-((6-tert.-butyl-2-(cyclohexylthio)pyridin-3-yl)methyl)-2-(3-fluoro-4-(N-methylmethylsulfonamido)phenyl)propanamide,
[12] 2-(3-fluoro-4-(N-methylmethylsulfonamido)phenyl)-N-(2-(4-methylpiperidin-1-yl)-4-(trifluoromethyl)benzyl)propanamide,
[13] N-(2-(cyclohexylthio)-4-(trifluoromethyl)benzyl)-2-(3-fluoro-4-(N-methylmethylsulfonamido)phenyl)propanamide,
[14] N-(4-tert.-butyl-2-(4-methylpiperidin-1-yl)benzyl)-2-(3-fluoro-4-(N-methylmethylsulfonamido)phenyl)propanamide,
[15] N-(4-tert.-butyl-2-(cyclohexylthio)benzyl)-2-(3-fluoro-4-(N-methylmethylsulfonamido)phenyl)propanamide, The following Table 1 states the measured mass spectrometry values for the additional example compounds.

| Example Compound | [M + H] |
| --- | --- |
| 4 | 421 |
| 5 | 421 |
| 6 | 435 |
| 7 | 548 |
| 8 | 562 |
| 9 | 545 |
| 10 | 519 |
| 11 | 536 |
| 12 | 530 |
| 13 | 547 |
| 14 | 518 |
| 15 | 535 |

Pharmacological Data

The affinity of the compounds according to the invention for the vanilloid receptor 1 (VR1/TRPV1 receptor) was determined as described above (Pharmacological methods I or II).

The compounds according to the invention of the above-stated formula I exhibit excellent affinity for the VR1/TRPV1 receptor (Table 2).

TABLE 2

| Compound according to Example | $K_i$ (rat) Capsaicin [nM] | $K_i$ (human) Capsaicin [nM] | $IC_{50}$ (human) [nM] after pH stimulus |
| --- | --- | --- | --- |
| 1 | 19.5 | 69.1 | 524.5 |
| 2 | 2.2 | 11.9 | 947 |
| 3 | 20 | 55.5 | 16% @ 10 µM; 8% @ 5 µM |
| 4 | 50.4 | Ne | 22% @ 10 µM; 0% @ 5 µM |
| 6 | 66.8 | Ne | 21% @ 10 µM; 0% @ 5 µM |
| 7 | 30.8 | 48.1 | 20% @ 10 µM; 0% @ 5 µM |
| 9 | 63.8 | 22.7 | 46% @ 10 µM; 11% @ 5 µM |
| 10 | 2.8 | 27.7 | 11% @ 10 µM; 0% @ 5 µM |
| 11 | 16.8 | 56% @ 5 µM; 33% @ 1 µM; 0% @ 0.1 µM | ne |
| 12 | 5.0 | 7.8 | 43% @ 10 µM; 0% @ 5 µM |
| 13 | 5.2 | 33.1 | ne |
| 14 | 3 | 13.1 | 43% @ 10 µM; 9% @ 5 µM |
| 15 | 7.6 | 18.3 | 30% @ 10 µM; 6% @ 5 µM; 0% @ 1 µM | ne means in each case "no effect", i.e. no response was observed.
The value after the sign "@" indicates the concentration at which inhibition (in percent) was determined in each case.

The value after the sign "@" indicates the concentration at which inhibition (in percent) was determined in each case.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents.

What is claimed is:

1. A compound corresponding to formula I:

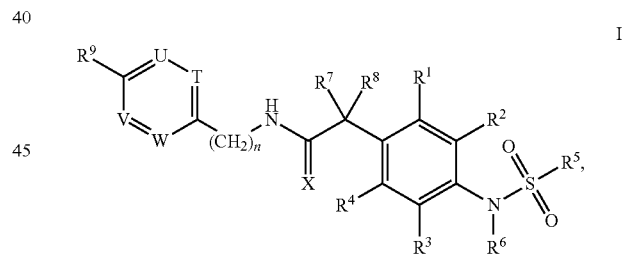

wherein:
X represents O;
n is 1;
$R^1$, $R^3$ and $R^4$ each represent H;
$R^2$ represents F; Cl or Br;
$R^5$ represents an alkyl residue selected from the group consisting of methyl, ethyl, n-propyl and isopropyl;
$R^5$ represents —C(=O)—$R^{28}$ or a residue selected from the group consisting of methyl, —CH$_2$—CN, ethyl, —CH$_2$—CH$_2$—CN, n-propyl, —CH$_2$—CH$_2$—CH$_2$—CN, n-butyl, —CH$_2$—CH$_2$-CH$_2$—CH$_2$—CN, sec.-butyl, isobutyl, tert. butyl and n-pentyl;
$R^7$ represents an alkyl residue selected from the group consisting of —CH$_2$—OH, —CH$_2$—CH$_2$—OH, —CH$_2$—CH$_2$—CH$_2$—OH, —CH$_2$—CH$_2$—CH$_2$—CH$_2$—OH, isopropyl, n-butyl, sec.-butyl, isobutyl, methyl, ethyl and n-propyl;

R[8] represents hydrogen;
T denotes C—R[29]; U denotes C—R[30]; V denotes C—R[31], and W denotes C—R[32],
R[9] represents —CF$_3$; or tert.-butyl;
R[28] represents a residue selected from the group consisting of methyl, ethyl, n-propyl, isopropyl, sec.-butyl, isobutyl, tert.-butyl, ethenyl and propenyl;
R[29], R[30] and R[31] each represent H;
R[32] represents —NHR[33]; —NR[34]R[35]; —OR[36] or —SR[37];
R[33], R[36] and R[37] each independently represent a residue selected from the group consisting of cyclopropyl, cyclobutyl, cyclopentyl, cyclohexyl and cycloheptyl, which optionally may be substituted with 1, 2, 3, 4 or 5 substituents independently selected from the group consisting of methyl, ethyl, n-propyl, isopropyl, n-butyl, sec.-butyl, isobutyl, tert.-butyl, n-pentyl;
R[34] and R[35] together with the nitrogen atom to which they are attached form a residue selected from the group consisting of pyrrolidinyl, piperidinyl, piperazinyl, morpholinyl and azepanyl, wherein the heterocycloaliphatic moiety may be unsubstituted or optionally substituted with 1, 2, 3, 4 or 5 residues R[51];
R[51] represents —NHR[52], —NR[53]R[54] or an alkyl residue selected from the group consisting of methyl, ethyl, n-propyl, isopropyl, tert.-butyl, n-butyl, sec.-butyl and isobutyl;
R[52], R[53] and R[54] each independently represent —C(=O)—R[55]; or an alkyl residue selected from the group consisting of methyl, ethyl, n-propyl, isopropyl, tert.-butyl, n-butyl, sec.-butyl, and isobutyl; or
a phenyl residue, wherein the phenyl residue may be substituted with 1, 2, 3, 4 or 5 substituents independently selected from the group consisting of F, Cl, Br, methyl, ethyl, n-propyl and isopropyl; and
R[55] represents an alkyl residue selected from the group consisting of methyl, ethyl, n-propyl, isopropyl, tert.-butyl, n-butyl, sec.-butyl, and isobutyl;
or a salt thereof.

2. A compound according to claim 1, wherein said compound is in the form of an isolated stereoisomer.

3. A compound according to claim 1, wherein said compound is in the form of a mixture of stereoisomers in any mixing ratio.

4. A compound according to claim 1, wherein said compound is in the form of a racemic mixture.

5. A compound according to claim 1, wherein said compound corresponds to formula Ia:

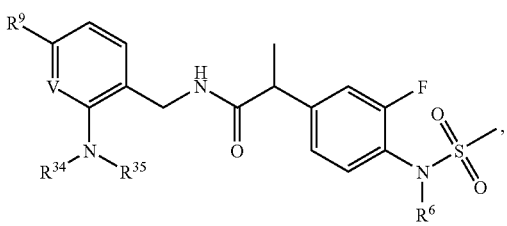

wherein
V denotes CH; and
R[6], R[9], R[34] and R[35] have the respective meanings given in claim 1;
or a salt thereof.

6. A compound according to claim 1, wherein said compound corresponds to formula Ib:

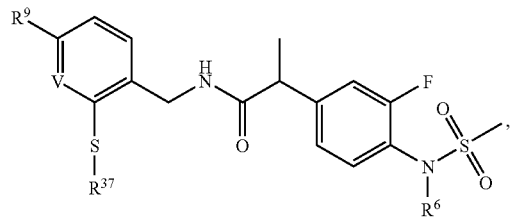

wherein
V denotes CH; and
R[6], R[9] and R[37] have the respective meanings given in claim 1;
or a salt thereof.

7. A compound according to claim 1, wherein said compound is selected from the group consisting of:
[12] 2-(3-fluoro-4-(N-methylmethylsulfonamido)phenyl)-N-(2-(4-methylpiperidin-1-yl)-4-(trifluoromethyl)benzyl)propanamide,
[13] N-(2-(cyclohexylthio)-4-(trifluoromethyl)benzyl)-2-(3-fluoro-4-(N-methylmethylsulfonamido)phenyl)propanamide,
[14] N-(4-tert.-butyl-2-(4-methylpiperidin-1-yl)benzyl)-2-(3-fluoro-4-(N-methylmethylsulfonamido)phenyl)propanamide, and
[15] N-(4-tert.-butyl-2-(cyclohexylthio)benzyl)-2-(3-fluoro-4-(N-methylmethylsulfonamido)phenyl)propanamide,
or a salt thereof.

8. A compound according to claim 1, wherein, in a FLIPR assay with CHO K1 cells transfected with the human gene VR1, said compound at a concentration of less than 2000 nM, brings about a 50% displacement of capsaicin which is present in a concentration of 100 nM.

9. A compound according to claim 8, wherein said compound at a concentration of less than 300 nM, brings about a 50% displacement of capsaicin which is present in a concentration of 100 nM.

10. A compound according to claim 8, wherein said compound at a concentration of less than 75 nM, brings about a 50% displacement of capsaicin which is present in a concentration of 100 nM.

11. A compound according to claim 8, wherein said compound at a concentration of less than 10 nM, brings about a 50% displacement of capsaicin which is present in a concentration of 100 nM.

12. A pharmaceutical composition comprising a compound according to claim 1, and at least one pharmaceutically acceptable carrier or pharmaceutical auxiliary substance.

13. A method of producing a compound according to claim 1, said method comprising:
reacting a compound corresponding to formula II:

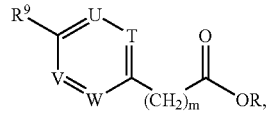

wherein R⁹, U, T, V, and W have the respective meanings given in claim 1,
m is 1, and
R represents hydrogen or a linear or branched $C_{1-6}$ alkyl residue,
in a reaction medium, in the presence of at least one reducing agent,
to yield a compound corresponding to formula III:

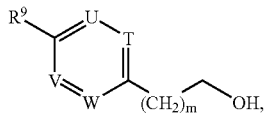

III wherein R⁹, U, I, V, W and m have the respective meanings given above, and optionally isolating or purifying the compound of formula III;
  reacting the compound corresponding to formula III in a reaction medium in the presence of diphenylphosphoryl azide or $HN_3$ to yield a compound corresponding to formula IV:

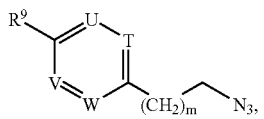

IV wherein R⁹, U, T, V, W and m have the respective meanings given above,
  and optionally isolating or purifying the compound of formula IV;
  reacting the compound of formula IV
in a reaction medium in the presence of a reducing agent, or
in a reaction medium in the presence of a catalyst and of hydrogen or hydrazine, or
in a reaction medium in the presence of triphenylphosphine to yield a compound corresponding to formula V:

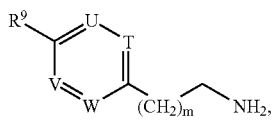

V wherein R⁹, U, T, V, W and in have the respective meanings given above;
  or
  reacting a compound corresponding to formula VI:

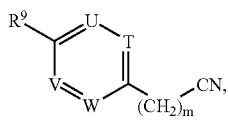

VI wherein R⁹, U, T, V, W and m have the respective meanings given above, in a reaction medium,
in the presence of a catalyst under a hydrogen atmosphere, optionally in the presence of an acid, or
in the presence of at least one reducing agent selected from the group consisting of $BH_3.S(CH_3)_2$, lithium aluminium hydride and sodium borohydride, optionally in the presence of $NiCl_2$,
to yield a compound corresponding to formula V or a salt thereof;
  and optionally isolating or purifying the compound of formula V;
  reacting the compound corresponding to formula V with a compound corresponding to formula VII:

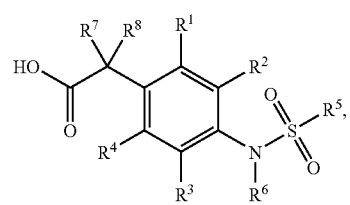

VII wherein
R¹, R², R³, R⁴, R⁵, R⁶, R⁷ and R⁸ have the respective meanings given in claim 1, and R⁶ may additionally represent hydrogen,
in a reaction medium, optionally in the presence of a coupling agent, and optionally in the presence of a base;
or with a compound corresponding to formula VIII:

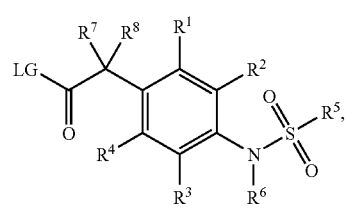

VIII wherein R¹, R², R³, R⁴, R⁵, R⁶, R⁷ and R⁸ have the respective meanings given above, and LG denotes a leaving group,
in a reaction medium, and optionally in the presence of at least one base, to yield a compound corresponding to formula Ih:

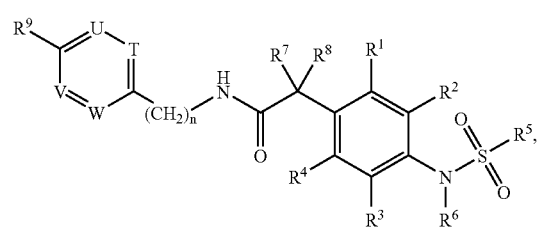

Ih wherein
T, U, V, W, R¹, R², R³, R⁴, R⁵, R⁶, R⁷, R⁸ and R⁹ have the respective meanings given in claim 1; R⁶ may additionally represent hydrogen, and n is 1, 2, 3 or 4, and optionally isolating or purifying the compound of formula Ih; and
  optionally reacting the compound of formula Ih in a reaction medium with a compound corresponding to formula IX:

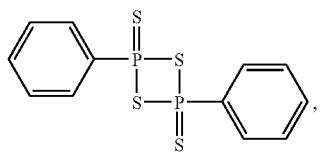

wherein each of the phenyl residues is substituted with 1 or 2 substituents independently selected from the group consisting of methoxy, phenoxy, Cl, methyl and Br,
or with phosphorus pentasulfide,
to yield a compound corresponding to formula Ik:

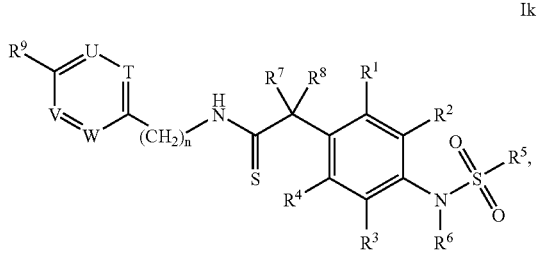

wherein T, U, V, W, $R^1$, $R^2$, $R^3$, $R^4$, $R^5$, $R^6$, $R^7$, $R^8$, $R^9$ and n have the respective meanings given above, optionally isolating or purifying the compound of formula Ik;
and—optionally reacting a compound corresponding to formula Io:

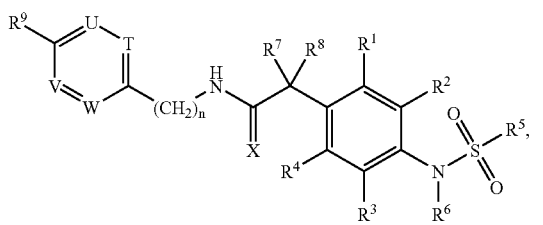

wherein X, T, U, V, W, $R^1$, $R^2$, $R^3$, $R^4$, $R^5$, $R^7$, $R^8$, $R^9$ and n have the respective meanings given above,
in a reaction medium, in the presence of n compound corresponding to the formula

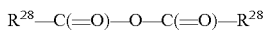

$R^{28}$—C(=O)—O—C(=O)—$R^{28}$ wherein $R^{28}$ has the meaning given in claim 1,
to yield a compound of formula I,
wherein X, T, U, V, W, $R^1$, $R^2$, $R^3$, $R^4$, $R^5$, $R^7$, $R^8$ and $R^9$ have the respective meanings given in claim 1; $R^6$ denotes —C(=O)—$R^{28}$, and n is 1, 2, 3 or 4, and optionally isolating or purifying the compound of formula I.

14. A method according to claim 13, wherein the compound of formula II is reacted in the presence of at least one reducing agent selected from the group consisting of sodium hydride, sodium, potassium hydride, lithium aluminium hydride, sodium borohydride and di(isobutyl)aluminium hydride; or wherein the compound of formula IV is reacted in the presence of at least one reducing agent selected from the group consisting of sodium hydride, potassium hydride, lithium aluminium hydride, sodium borohydride and di(isobutyl)aluminium hydride; or wherein the compound of formula IV is reacted in the presence of a platinum or palladium catalyst; or wherein a compound corresponding to formula VI is reacted in the presence of a palladium or platinum catalyst and of hydrochloric acid; or wherein LG denotes a chlorine or bromine atom; or wherein each of the phenyl groups in the compound of formula IX is substituted by 1 or 2 phenoxy or methoxy residues.

15. A method of producing a compound according to claim 1, said method comprising:
reacting a compound corresponding to formula X:

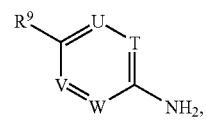

wherein $R^9$, U, T, V and W have the respective meanings given in claim 1, with a compound corresponding to formula VII:

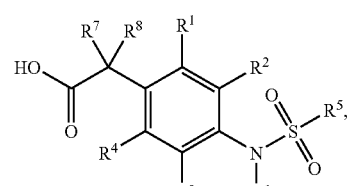

wherein $R^1$, $R^2$, $R^3$, $R^4$, $R^5$, $R^6$, $R^7$ and $R^8$ have the respective meanings given in claim 1, and $R^6$ may additionally represent hydrogen,
in a reaction medium, optionally in the presence of a coupling agent, and optionally in the presence of a base,
or with a compound corresponding to formula VIII:

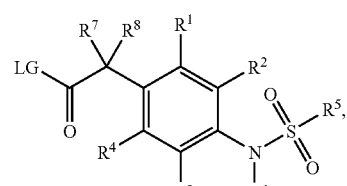

wherein $R^1$, $R^2$, $R^3$, $R^4$, $R^5$, $R^6$, $R^7$ and $R^8$ have the respective meanings given above, and LG denotes a leaving group, in a reaction medium, and optionally in the presence of a base, to yield a compound corresponding to formula Im:

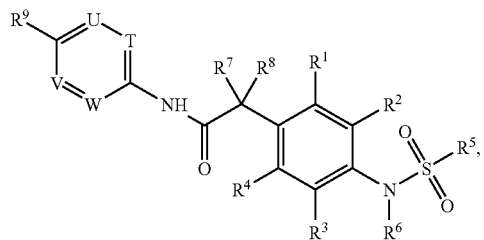

wherein T, U, V, W, $R^1$, $R^2$, $R^3$, $R^4$, $R^5$, $R^7$, $R^8$ and $R^9$ have the respective meanings given above, and optionally isolating or purifying the compound of formula Im; and optionally reacting a compound corresponding to formula Im in a reaction medium with a compound corresponding to formula IX:

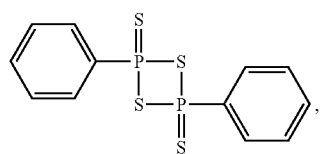

wherein each of the phenyl residues is substituted with 1 or 2 substituents independently selected from the group consisting of methoxy, phenoxy, Cl, methyl and Br, or with phosphorus pentasulfide, to yield a compound corresponding to formula In:

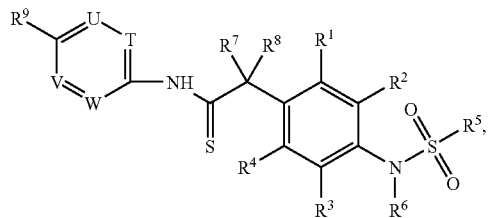

wherein T, U, V, W, $R^1$, $R^2$, $R^3$, $R^4$, $R^5$, $R^6$, $R^7$, $R^8$ and $R^9$ have the respective meanings given above, and optionally isolating or purifying the compound of formula In; and optionally reacting a compound corresponding to formula Ip:

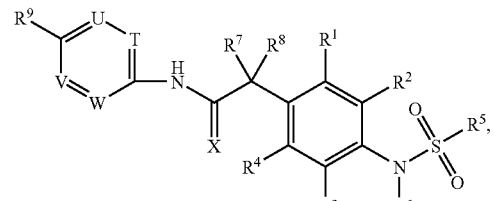

wherein X, T, U, V, W, $R^1$, $R^2$, $R^3$, $R^4$, $R^5$, $R^7$, $R^8$ and $R^9$ have the respective meanings given above, in a reaction medium and in the presence of a compound corresponding to the formula:

$$R^{28}-C(=O)-O-C(=O)-R^{28}$$

wherein $R^{28}$ has the meaning given in claim 1, to yield a compound of formula I, wherein X, T, U, V, W, $R^1$, $R^2$, $R^3$, $R^4$, $R^5$, $R^7$, $R^8$ and $R^9$ have the meanings given above and $R^6$ represents $-C(=O)-R^{28}$, and optionally isolating or purifying the compound of formula I.

16. A method according to claim 15, wherein LG denotes a chlorine or bromine atom; or wherein each of the phenyl groups in the compound of formula IX is substituted with 1 or 2 phenoxy or methoxy residues; or wherein each of the phenyl groups in the compound of formula IX is substituted with a methoxy residue in the para position.

17. A method of treating or inhibiting pain in a subject, said method comprising administering to said subject a pharmacologically effective amount of a compound according to claim 1.

18. A method according to claim 17, wherein said pain is selected from the group consisting of acute pain, chronic pain, neuropathic pain, visceral pain, joint pain, hyperalgesia, allodynia, causalgia and migraine.

\* \* \* \* \*